Figure 1:
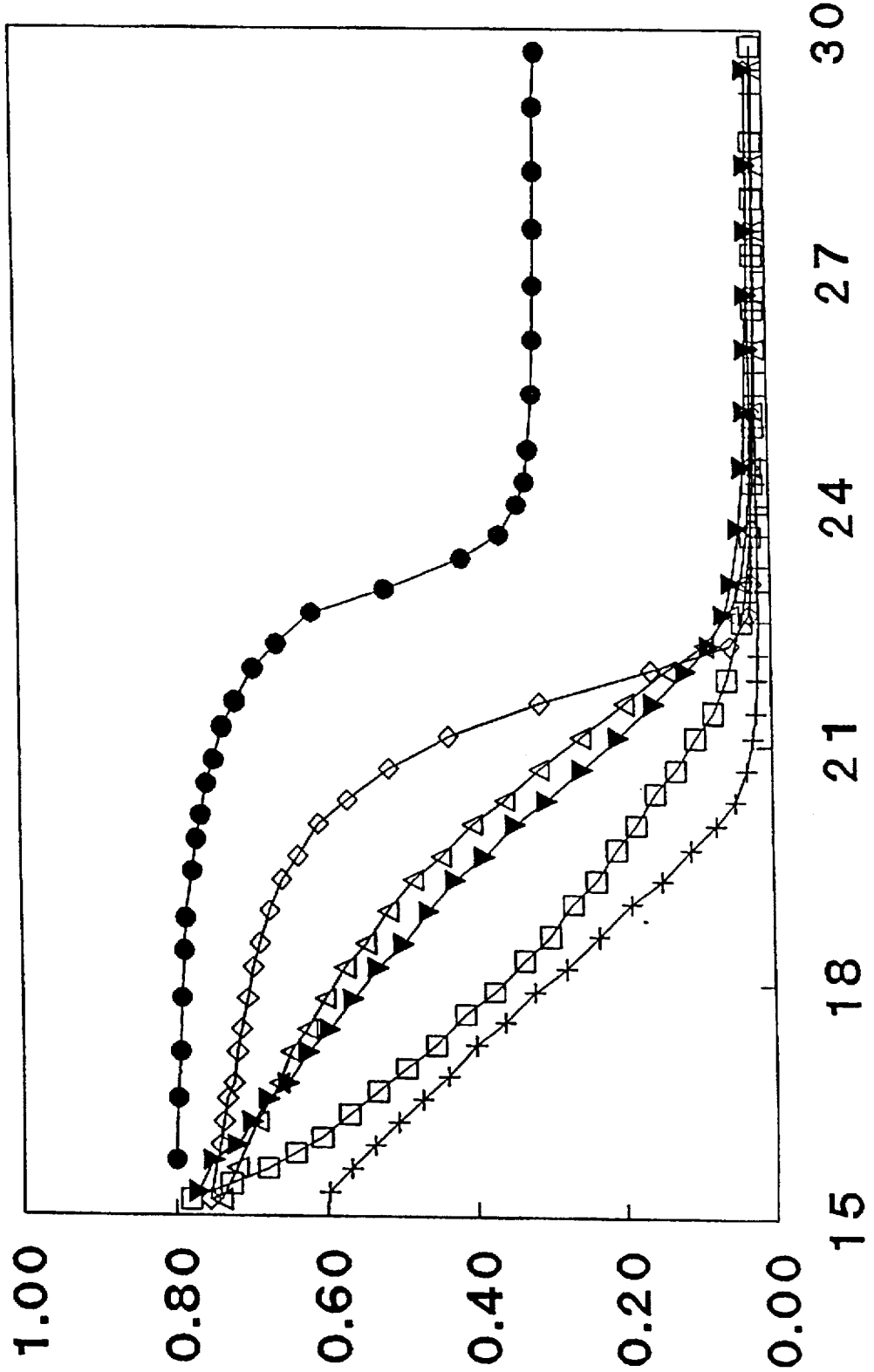

United States Patent [19]

Rosseneu et al.

[11] Patent Number: 5,733,879
[45] Date of Patent: Mar. 31, 1998

[54] PEPTIDES AND PROTEINS, PROCESS FOR THEIR PREPARATION AND THEIR USE AS CHOLESTEROL ACCEPTORS

[75] Inventors: Maryvonne Rosseneu, Brugge; Robert Brasseur, Haillot; Robert Deleys, Grimbergen; Christine Labeur, Brugge, all of Belgium

[73] Assignee: N.V. Innogenetics, S.A., Ghent, Belgium

[21] Appl. No.: 351,423

[22] PCT Filed: Jun. 8, 1993

[86] PCT No.: PCT/EP93/01444

§ 371 Date: Dec. 23, 1994

§ 102(e) Date: Dec. 23, 1994

[87] PCT Pub. No.: WO93/25581

PCT Pub. Date: Dec. 23, 1993

[30] Foreign Application Priority Data

Jun. 12, 1992 [EP] European Pat. Off. ............ 92 401 621

[51] Int. Cl.⁶ ............................ G01N 33/53; A61K 38/00
[52] U.S. Cl. ........................ 514/13; 514/12; 514/21; 530/324; 530/326; 530/359
[58] Field of Search ........................ 514/12, 13, 21; 530/326, 359, 324

[56] References Cited

U.S. PATENT DOCUMENTS 5,177,189  1/1993  Dyer et al. ............... 514/12
5,182,364  1/1993  Dyer et al. ............... 530/324

FOREIGN PATENT DOCUMENTS

WO 91/02751  6/1991  WIPO.
9102751  7/1991  WIPO.

OTHER PUBLICATIONS

Epand et al. J. Biol. Chem. vol. 264:8, Mar. 1989, pp. 4628–4635.
Brasseur et al. J. Biol. Chem., vol. 266: 24, 25, Aug. 1991, pp. 16120–16127.
Journal of Biological Chemistry, vol. 264, No. 8, 15 Mar. 1989, Baltimore, U.S., pp. 4628–4635, Epand et al, 'Properties of lipid complexes with amphipatic helix–forming peptides' cited in the application.
Journal of Biological Chemistry, vol. 266, No. 24,25 Aug. 1991, pp. 16120–16127, Brasseur 'Differentiation of lipid–associating helices by use of three–dimensional molecular hydrophobicity et al'.
Srinivas RV, et al. Journal of Cellular Biochemistry 45:224–237 (1991) "Inhibition of Virus–Induced Cell Fusion by Apolipoprotein A–I and its Amphipathic Peptide Analogs".
Jorgensen EV et al. The Journal of Biological Chemistry, 264 (16) 9215–9219 (1989) "Synthetic Amphipathic Peptides Resembling Apolipoproteins Stimulate Release of Human Placental Lactogen".
Epand RM et al. The Journal of Biological Chemistry 262(19) 9389–9396 (1987) "Studies of Synthetic Peptide Analogs of the Amphipathic Helix".

*Primary Examiner*—Cecilia J. Tsang
*Assistant Examiner*—Lynn Touzeau
*Attorney, Agent, or Firm*—Nixon & Vanderhye, P.C.

[57] ABSTRACT

The subject invention relates to amino acid sequences derived from peptide ($Glu^{1,8}$, $Leu^{11,17}$) 18A, comprising:

Glu-Trp-Leu-A-Ala-B-Tyr-C-Lys-Val-D-Glu-Lys-Leu-Lys-Glu-Leu-Phe, wherein A is Lys, Glu or Asp; B is Phe, Glu or Asp; C is Glu, Lys or Arg;

and D is Leu, Glu or Asp. The amino acid sequences form complexes with phospholipids, and are useful for the treatment of cardiovascular disease.

29 Claims, 24 Drawing Sheets

PEPTIDES AND PROTEINS, PROCESS FOR THEIR PREPARATION AND THEIR USE AS CHOLESTEROL ACCEPTORS

The present invention relates to new peptides and new proteins, to a process for their preparation, and to their use as cholesterol acceptors.

Atherosclerosis, and its attendant complications such as coronary heart disease in particular are among the most common and critical health problems today. A number of risk factors have been implicated in the development of "premature" atherosclerosis, one of the most important of these being elevated plasma cholesterol. Because of the crucial role that cholesterol appears to play in the occurrence of heart disease, a great deal of attention has been devoted to the study of its metabolism in the human body.

The major function of the apolipoproteins is to carry lipids including cholesterol, phospholipids and triglycerides in plasma and to deliver these lipids to a variety of cells (Pownall et al., 1987; Kovanen et al., 1990). These lipid-apolipoprotein complexes constitute the different classes of the plasma lipoproteins. Most of the smaller water-soluble apolipoproteins have a high alpha-helical content, and contain several amphipathic segments with a high degree of homology (De Loof et al., 1987; Brasseur et al., 1990). Low density lipoproteins are involved in the delivery of cholesterol to peripheral cells (Brown et al., 1986; Gianturco et al., 1987), while high density lipoproteins (HDL) are responsible for the transport of excess cholesterol from the peripheral tissues to the liver, i.e., "reverse cholesterol transport". Several mechanisms have been proposed to account for the targeting of the HDL to the liver. These include the uptake of apoE-rich HDL1, the direct uptake of HDL2 after the enzymatic action of hepatic lipase on HDL3, and the transfer of cholesteryl esters from HDL2 to apoB containing lipoproteins under the action of the cholesteryl ester transfer protein (CETP). Lecithin cholesterol acyl transferase (LCAT) and lipoprotein lipase (LPL) are enzymes which play major roles in the conversion of the nascent discoidal HDL and of the small HDL3 particles, which act as acceptors of cholesterol from peripheral cells, into larger HDL2 particles (Phillips et al., 1987). These are further catabolized, thus directing the flux of cholesterol to the liver. It has now been well documented (Delamatre et al., 1986) that apo AI, representing the major apoprotein constituent of HDL, is the major apoprotein involved in these processes.

Synthetic peptides, mostly 18–22 residues long, have been used as models for the study of helix-lipid interactions in an apolipophospholipid-protein complex (Sparrow and Gotto, 1981). The sequences of these amphipathic peptides either matched those of the helices of apo AI, AII or E (Fukushima et al., 1980) or represented consensus sequences for the various helical repeats identified in apo AI (Pownall et al., 1980; Anantharamaiah, 1986). The properties of these peptides and of the lipid-peptide complexes have been extensively studied and compared with those of the native apolipoproteins (Segrest et al., 1983; Segrest et al., 1990).

The differences observed between the lipid-binding and LCAT activation properties of the synthetic 18-residue peptides and those of the native apolipoproteins were attributed to the lack of cooperativity between single peptides in the lipid-peptide complexes (Fukushima et al., 1980).

The following sequence:

Glu-Trp-Leu-Lys-Ala-Phe-Tyr-Glu-Lys-Val-Leu-Glu-Lys-Leu-Lys-Glu-Leu-Phe has been derived from the 18A peptide described by the group of Segrest (Anantharamaiah, 1986; Segrest et al., 1990).

Although this peptide is an amphipathic lipid-associating peptide, nothing is demonstrated in the above-mentioned article with regard to a capacity of promoting cholesterol efflux from lipid-loaded cells. Epand et al. (1989) have described the LCAT activation and vesicle lysing properties of the peptide of formula:.

Glu-Trp-Leu-Lys-Ala-Phe-Tyr-Glu-Lys-Val-Leu-Glu-Lys-Leu-Lys-Glu-Leu-Phe

The aim of the invention is to provide new peptides and proteins and phospholipid complexes thereof acting as acceptors and carriers for excess cholesterol.

The aim of the invention is also to provide new peptides and proteins and phospholipid complexes thereof which combine a maximal storage capacity for cholesterol and an optimal substrate efficiency for the lecithin cholesteryl acyl transferase (LCAT) enzyme, thereby driving the cholesterol efflux derived from peripheral cells maximally towards the liver.

The aim of the invention is also to provide drugs liable to be used for the treatment of cardiovascular diseases, and more specifically to remove cholesterol from atherosclerotic lesions. Furthermore such peptides and proteins and their phospholipid complexes could be used in the treatment of endotoxic shock, by means of binding LPS, as has been reported for HDL (Levine et al., 1992).

The invention relates to a peptide or a protein containing or constituted by a peptide derived from peptide 18A by substitution of one or several amino acids of peptide 18A, and/or deletion of one or several amino acids of peptide 18A, and/or addition of one or several amino acids of peptide 18A, with said peptide being different from peptide 18A and presenting the following characteristics:

it is coiled in the form of an alpha helix having from 2 Go 8, preferably 5 turns, each turn bearing 3.6 amino acid residues, the diameter of said helix is from about 13 Å to about 16 Å, preferably of about 15 Å, the distance separating two consecutive turns of said helix being from about 4 Å to about 6 Å, preferably of about 5 Å, the length of the helix being from about 10 Å to about 30 Å, preferably from about 24 Å to about 26 Å, and more preferably of about 25 Å, it is amphipathic, the value of the hydrophobic pho angle is from about 120° to about 180°, preferably from about 140° to about 180°, the value of the hydrophilic phi angle is from about 180° to about 240°, preferably from about 180° to about 220°, with said peptide being such that either the amino acid in position 4 is Glu or Asp and/or the amino acid in position 6 is Glu or Asp and/or the amino acid in position 8 is Lys or Arg and/or the amino acid in position 11 is Glu or Asp.

All the above-mentioned parameters, i.e., number of turns, number of amino acid residues, diameter of the helix, distance between two consecutive turns and length of the helix can be determined according to theoretical method calculations described in Brasseur et al. (1991).

The length of the helix depends on the number of turns which are formed. When the helix contains 5 turns, the length is normally between 24 Å and 26 Å.

The hydrophobic pho angle is determined as follows: in an Edmundson wheel projection of the helices, most of the hydrophobic residues are situated in one region determining the hydrophobic side of the helix. The calculation of the molecular hydrophobic potential along the axis of the helix is as proposed by Brasseur et al.(1991), and its projection onto a plane perpendicular to the axis of the helix enables the calculation of the angle pho. This angle represents the hydrophobic area of the helix. The hydrophilic angle phi is the complement of the pho angle: 360°-pho.

The expression amphipathic means that there is a segregation of the hydrophilic and hydrophobic areas on opposite faces of the helix. The amphipathic helical moment (μH) can be determined according to the method of Eisenberg (Eisenberg, 1984; Eisenberg et al., 1984).

In the peptides of the invention, at least one of the termini of the peptides is advantageously blocked. Advantageously both termini of the peptides are blocked by protecting groups.

The expression "both termini of the peptide are blocked" refers to any modification of the α-helix peptide ends which has been demonstrated to be beneficial to the stabilization of α-helices, more particularly a modification of the α-helix peptide ends which abolishes the existence of charges on the N- and C-terminal ends of the peptide as described for instance by Scholtz & Baldwin (1992). An example of the way such modifications are introduced into the peptides of the invention is given in the example section.

According to an advantageous embodiment, the above-defined proteins and peptides of the invention are such that the amino acids in position 1 and 16 are different from Asp and Glu and/or the amino acids in position 9 and 13 are different from Lys and Arg.

By way of example, the amino acid at position 1 can be: Ash, Gin, Tyr, Set, Thr, Arg, His, Lys or Ala, the amino acid at position 9 can be: Ash, Gin, Tyr, Set, Thr, His, Ala, Asp or Glu, the amino acid at position 13 can be: Ash, Gin, Tyr, Set, Thr, His, Ala, Asp or Glu, the amino acid at position 16 can be: Ash, Gin, Tyr, Set, Thr, Arg, His, Lys, or Ala.

According to an advantageous embodiment, the peptide or the protein of the invention contains or is constituted by a peptide as above-defined, with said peptide being able to bind or to associate with phospholipids or with phospolipids and cholesterol to form a discoidal complex together with other peptides which have the above-defined characteristics, with said peptides being such that in the above-said phospholipid-protein complex, each peptide is in the shape of an alpha helix containing from 2 to 8, preferably 5 turns, with each said turn containing 3.6 amino acid residues, the above-mentioned helix has a diameter from about 13 Å to about 16 Å, preferably of about 15 Å, the distance separating two consecutive turns of said helix being from about 4 Å to about 6 Å, preferably of about 5 Å, the length of the helix being from about 10 Å to about 30 Å, preferably from about 24 Å to about 26 Å and more preferably of about 25 Å, it is amphipathic, the value of the hydrophobic pho angle ranges from about 120° to about 180°, preferably from about 140° to about 180°, the value of the hydrophilic phi angle ranges from about 180° to about 220°, preferably from about 180° to about 220°, each peptide contains at least one amino acid liable to interact in an ionic bond with the opposite amino acid of the contiguous anti-parallel helix constituted by one of its adjacent peptides and the distance between the opposite amino acids involved in this ionic bond is less than about 10 Å, preferably from about 6 Å to about 8 Å, and more preferably less than 5 Å, the energy of interaction between the above-mentioned amino acids is at east +5 kcal/mole and preferably from −10 kcal/mole to −1 kcal/mole.

It is to be noted that each peptide in the discoidal complex is linked through ionic bonds with its two adjacent peptides.

The expression "above-defined characteristics" corresponds to the number of turns, the diameter of the helix, the distance separating two consecutive turns, the length of the helix, the value of the hydrophobic pho angle, the hydrophilic phi angle, as well as the amphipathic property.

The peptides and proteins of the invention are such that the above-defined peptides are disposed with respect to each other such as to form a disc inside which the phospholipids are found, the peptides and phospholipids thus forming a discoidal complex; in said complex, the phospholipids are associated with the peptides through hydrophobic interactions and the peptides are linked between one another through hydrophobic and hydrophilic interactions, and particularly through ionic bonds created between the charged amino acid of one peptide and the opposite charged amino acids of the adjacent peptide, characterized by their electrostatic energy of interaction. The blocked amino- and carboxy terminal do not contribute to this electrostatic energy of interaction.

The amino acids of one peptide and of its corresponding adjacent peptide are associated in pairs, the number of pairs being of at least one and preferably two, and two adjacent peptides are such that they preferably are oriented anti-parallel with respect to each other.

The distance between the opposite pairs can be evaluated through molecular modelling of a pair of peptides by the energy minimization techniques (Brasseur, 1991). The energy of interaction between two of the above-mentioned peptides can be calculated as the sum of the hydrophobic, Van der Waals and ionic interaction energies according to standard equations (Brasseur, 1991).

According to an advantageous embodiment, the peptide or protein of the invention is constituted by the above-defined peptide, which is part of a phospholipid-protein complex together with other peptides of the invention which are preferably identical to said peptide, with said complex containing from about 15 to about 25, preferably 20 peptides, and with said complex presenting a thickness of about 38 Å to about 42 Å, preferably of about 40 Å, and a diameter of about 80 Å to about 150 Å, preferably of about 80 Å to about 120 Å, the diameter being estimated by non-denaturating gradient polyacrylamide gel electrophoresis.

In the term "phospholipid protein complex", protein is to be understood as designating a protein but will preferably designate a peptide.

The number of peptides in a phospholipid-protein complex can be determined by measuring the phospholipid and the peptide concentrations. Together with the diameter of the complex determined by gradient gel electrophoresis and the diameter of the peptides derived from the molecular modelling, the number of peptides per complex can be calculated.

According to an advantageous embodiment, the peptides and proteins of the invention are such that the peptides are dimeric in form. Said dimers are such that the respective helices of each of the peptides are linked, advantageously by a beta-strand structure, with said structure preferably containing 5 amino acids, among which one of them can be a proline, preferably at position 3 from the N or C terminal part, with this dimer being possibly closed by a sequence preferably situated at the C- or N-terminal end, such as X-X-Cys-Cys-X-X, X being valine, alanine, glycine and more preferably glycine.

According to another embodiment, the peptides or proteins of the invention are such that in the above-defined discoidal complex:

when the peptide is associated with phospholipids, and in addition possibly with cholesterol, it can activate LCAT in an amount not less than about 10% of the LCAT activation by complexes prepared with native plasma apo AI-phospholipid complexes, and preferably from about 20% to about 40%, with this activation being measured using a substrate preparation consisting of a complex of PLPC/cholesterol/peptide in the molar ratio of 10/1/1 prepared for instance by cholate dialysis, with LCAT activity being expressed in nmoles of cholesteryl ester/h/ml of LCAT enzyme, with cholesteryl ester being for instance cholesteryl linoleate and being measured by HPLC (Vercaemst et at., 1989).

The phospholipid is advantageously PLPC (defined later).

The native plasma apo AI is purified from human plasma. Said purification can be done according to standard procedures including preparative ultracentrifugation, delipidation and fractionation on a MonoQ FPLC column.

Another substrate preparation can include DPPC (defined later) or POPC (defined later) as phospholipid, with a cholesterol concentration from 0 to 10% (weight percentage of the phospholipid), containing either apo AI or apo AIV (native apo AIV prepared from human plasma, according to the same technique as for apo AI).

The polypeptide or protein of the invention advantageously is such that the above-mentioned peptide presents the following characteristics:

when it is associated in a complex with phospholipids, and in addition possibly with cholesterol, it is stable against GdmCl denaturation, up to 4M of GdmCl, and advantageously in the range of 2M to 4M of GdmCl, measured according to Trp fluorescence emission, after excitation at 295 mm, it has a binding capacity for phospholipids from about 3 moles of phospholipids/mole of peptide to about 9 moles of phospholipids/mole of peptide and preferably of about 5 moles of phospholipids/mole of peptide, it has an alpha-helical content increase such that the difference between the free peptide and the peptide in the phospholipid-complex is of at least 15% measured by infrared spectroscopy or circular dichroism.

GdmCl means guanidium chloride.

Infrared will also be designated by IR and circular dichroism will also be designated by CD.

In the proteins and polypeptides of the invention, the percentage of the alpha-helix structure in the free peptide (not involved in a complex of the invention) is from about 20% to about 30% and in the phospholipid-protein complexes, the percentage of alpha-helix of the peptide is from about 40% to about 65% as determined by IR and circular dichroism measurements.

The increase of alpha-helical structure corresponds to a stabilization of the amphipathic helix by the lipids. The proteins and peptides of the invention are preferably used with both termini blocked.

The protein or polypeptide of the invention is such that the above-mentioned peptide presents the following characteristic when it is associated with phospholipids:

it induces a maximal cholesterol efflux under the form of free cholesterol from cholesterol-loaded cells of about 30% to about 50% (weight percentage), preferably of about 40% of the total cholesterol contained in the cells, at a peptide concentration in the complex of about 100 µg/ml. This corresponds to an amount of 5–25 µg of free cholesterol, and preferably 25 µg of free cholesterol released into the medium when 100 µg/ml complex is presented to the lipid-loaded cells.

The cholesterol remaining in the cell, either free or esterified, is measured by HPLC quantification.

The cholesterol efflux (cholesterol released into the medium) is measured enzymatically.

The cells can be of different origin.

Alternatives to the murine macrophages are human macrophage cell lines (THP-1), murine peritoneal macrophages, human macrophages isolated from peripheral blood, endothelial, adipocyte, or smooth muscle cell lines either from murine or human origin.

The free cholesterol liberated from the cells is incorporated into the phospholipid-protein complexes, which remain in the cell culture media. When an LCAT preparation is added together with the peptide-phospholipid complexes in the culture media, the cholesterol taken up from the cells as free cholesterol is immediately esterified in the complexes by the action of the LCAT which was added.

Advantageous proteins of the invention contains at least any one of the peptides of the following formulae:

M1 Glu-Trp-Leu-Lys-Ala-Phe-Tyr-Lys-Lys-Val-Leu-Glu-Lys-Leu-Lys-Glu-Leu-Phe (SEQ ID NO 1)

M2 Glu-Trp-Leu-Lys-Ala-Glu-Tyr-Glu-Lys-Val-Leu-Glu-Lys-Leu-Lys-Glu-Leu-Phe (SEQ ID NO 2)

M3 Glu-Trp-Leu-Lys-Ala-Glu-Tyr-Glu-Lys-Val-Glu Glu-Lys-Leu-Lys-Glu-Leu-Phe (SEQ ID NO 3)

M4 Glu-Trp-Leu-Glu-Ala-Phe-Tyr-Lys-Lys-Val-Leu-Glu-Lys-Leu-Lys-Glu-Leu-Phe (SEQ ID NO 4)

or are constituted by any one of said peptides.

According to an advantageous embodiment, the phospholipid-protein complex of the invention contains at least one of the abovedefined proteins or peptides, phospholipids and possibly cholesterol, with the mount of phospholipids being preferably from about 3 to about 9 moles per mole of the above-defined peptide, advantageously in a molar ratio of phospholipids, with respect to the above-defined peptide, varying from 2/1 to 4/1, and the mount of cholesterol being from 0 to 10% (weight percentage) with respect to the mount of phospholipids (w/w).

According to an advantageous embodiment, the phospholipid-protein complex of the invention presents a turbidity decrease with respect to dimyristoyl phosphatidylcholine (DMPC) of about 0.7 to about 0.05 at 340 nm when the protein is mixed with multilamellar DMPC liposomes and the mixture is heated from 15° C. to 25° C.

The phospholipid-protein complexes of the invention are such that they are advantageously stacked upon one another.

This is visible after negative staining with phosphotungstate in electromicrographs in which the discs are seen stacked upon one another in typical rouleaux that are variable in length. To give an idea, the number of stacked discs is from about 15 to about 70.

In the phospholipid-protein complexes of the invention the phospholipid is chosen from among:

DMPC: (dimyristoylphosphatidylcholine),

DPPC: (dipalrnitoylphosphatidylcholine),

POPC: (palmitoyloleolylphosphatidylcholine),

PLPC: (palmitoyllinoleylphosphatidylcholine), or egg PC (egg phosphatidylcholine), and is more preferably DPPC.

A process for preparing a phospholipid-protein complex of the invention, comprises the following steps:

incubation of any one of the proteins as defined above, with phospholipids, and possibly cholesterol, preferably in a ratio of 3/1 (w/w) of phospholipid/peptide and 0 to 10% of cholesterol/phospholipid (w/w) in the presence of a detergent such as sodium cholate, to obtain a phospholipid-protein complex and with subsequent dialysis of the detergent and fractionation of said complex, for instance by gel filtration or by density gradient ultracentrifugation, in order to remove free protein, free phospholipids and possibly free cholesterol.

The proteins and the peptides of the invention can be prepared according to the classical techniques in the field of peptide synthesis.

The synthesis can be carried out in homogeneous solution or in solid phase.

For instance, the synthesis technique in homogeneous solution which can be used is the one described by Houben-weyl in the book entitled "Methode der organdschen chemie" (Method of organic chemistry) edited by E. Wunsch, vol. 15-1 et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The proteins and peptides of the invention are intended for use in the formation of synthetic high-density lipoprotein.

The phospholipid-protein complexes of the invention may be used as substitute high density lipoprotein in the plasma, giving at least the same protective effect against cardiovascular diseases as would native HDL. They can also be used in the treament of endotoxic shock.

The invention thus also relates to pharmaceutical compositions comprising, as active substance, any one of the phospholipid-protein complexes of the invention in association with a pharmaceutical vehicle which is physiologically appropriate.

The mode of administration of the phospholipid-protein complex is preferably parenteral, i.e., intravenous, intraperitoneal, intramuscular, or subcutaneous, with the intravenous administration being most preferred. The synthetic complexes may be administered alone, without a carrier vehicle; however, they may also be administered with pharmaceutically acceptable non-toxic carriers, the proportions of which are determined by the suitability and chemical nature of the particular carrier. For intravenous or intramuscular administration, they may be used in the form of a sterile solution containing other solutes, for example, sufficient saline or glucose to make the solution isotonic.

The proteins of the subject invention may also prove to be administrable by use of a continuous perfusion device, which should simplify the method of administration.

Advantageously, the pharmaceutical compositions of the invention contain from about 10 mg to about 100 mg, particularly about 50 mg of phospholipid per kg of body weight.

This corresponds to about 10 mg to about 125 mg, particularly to about 65 mg of phospholipid-protein complex of the invention per kg of body weight.

The phospholipid-protein complexes of the invention are useful for the preparation of a drug destined for the treatment of cardiovascular diseases such as severe stenosis of the coronary arteries and peripheral vascular diseases, by reducing the progression and inducing regression of the artherosclerotic plaques. The preparation can also be used in the treatment of endotoxic shock.

The examples which are hereafter given are for illustrative purposes and the present invention is not limited to these examples.

DESCRIPTION OF THE FIGURES AND OF THE TABLES

FIG. 1 represents the turbidity decrease (on the y-axis, expressed as E/Eo, with E being the turbidity measured at different temperature points and Eo being the turbidity measured at 15° C.) at 325 nm upon the formation of complexes with DMPC vesicles as a function of the temperature (°C.), (x-axis) and on which:

the curve with "+" corresponds to M2, the curve with squares corresponds to M1, the curve with triangles corresponds to M4, the curve with diamonds corresponds to M3, the curve with filled circles corresponds to Apo AI, the curve with the filed triangles corresponds to 18A.

FIG. 2a to FIG. 2f represent the turbidity decrease (on the y-axis expressed as E/Eo, with E being the turbidity measured at different temperature points and Eo being the turbidity measured at 15° C.) at 325 nm upon the formation of complexes with DMPC vesicles as a function of the temperature (on the x-axis) at different concentrations of sodium chloride.

The curves with squares correspond to a concentration of NaGl of 0.15M.

The curves with "+" correspond to a concentration of NaCl of 0.5M.

The curves with circles correspond to a concentration of NaCl of 0.8M.

Figure 2A:
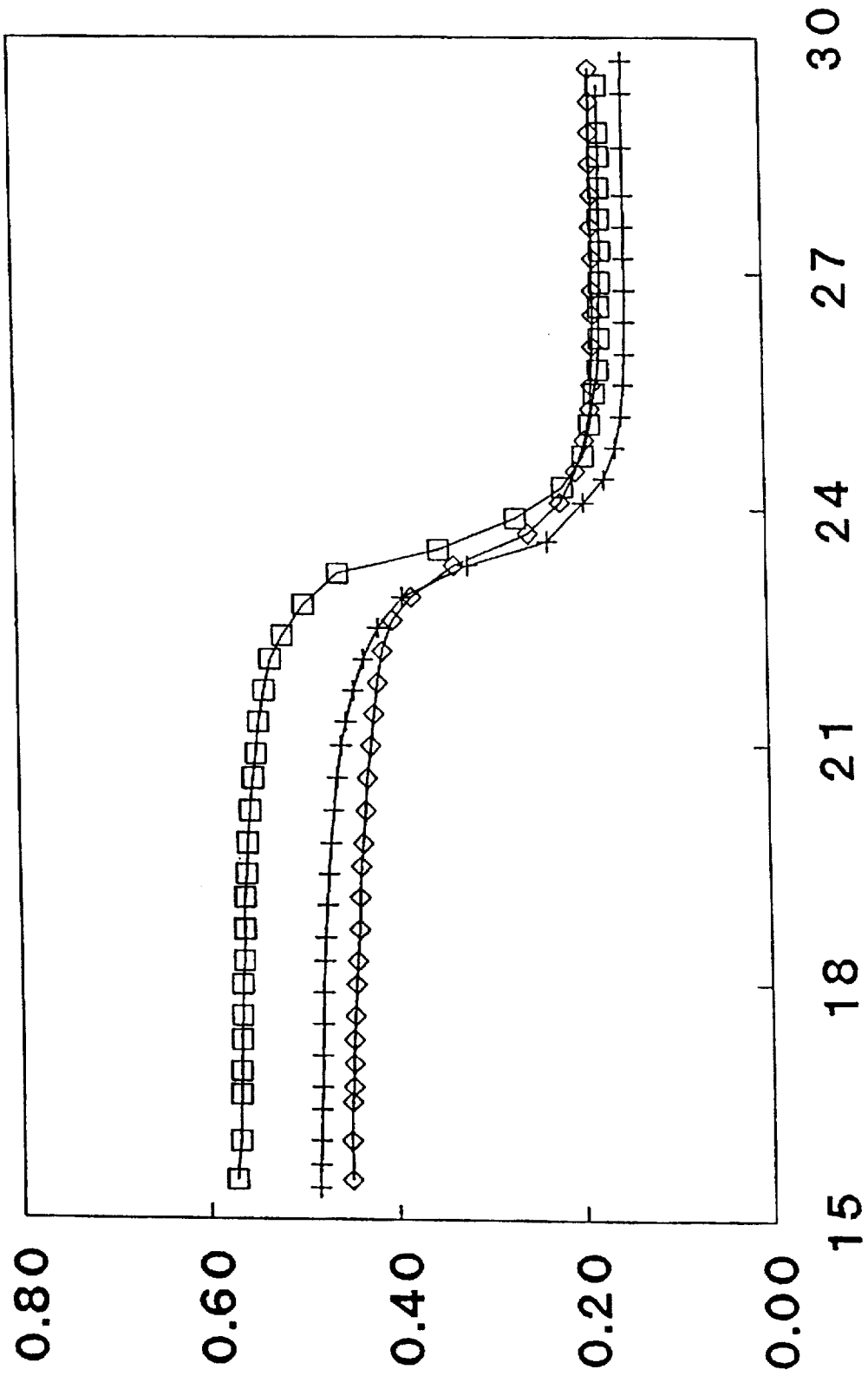
Figure 2B:
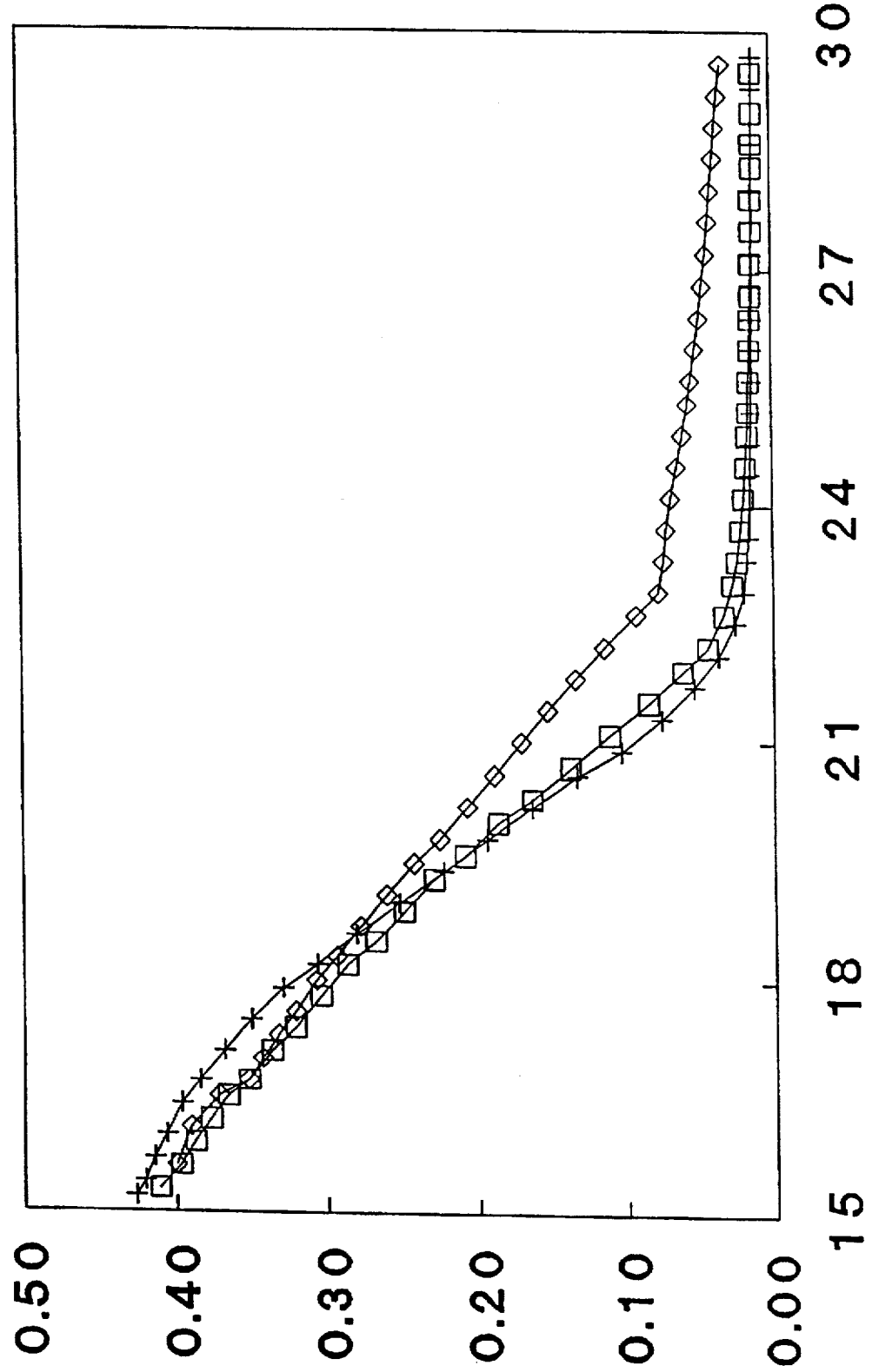
Figure 2C:
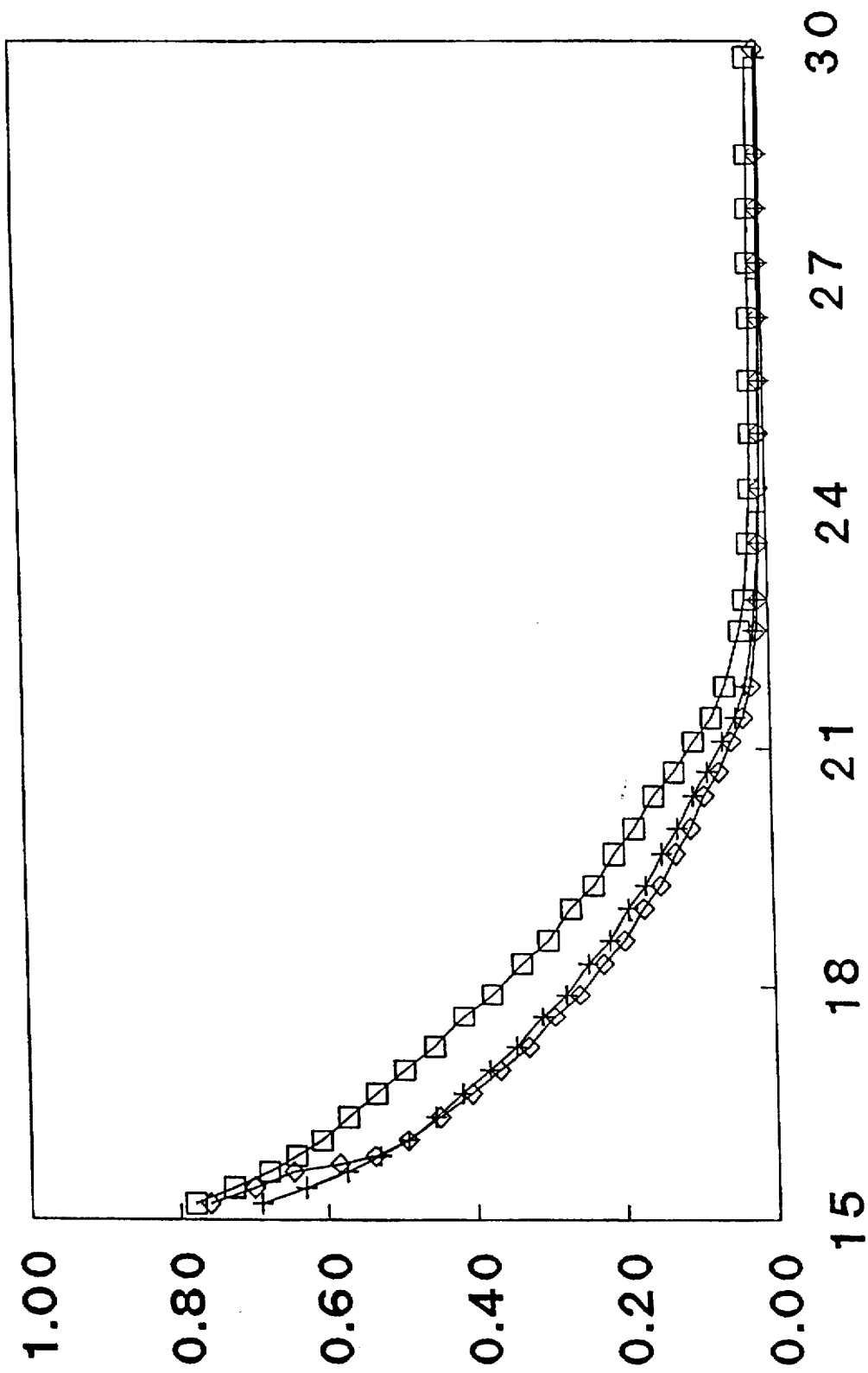
Figure 2D:
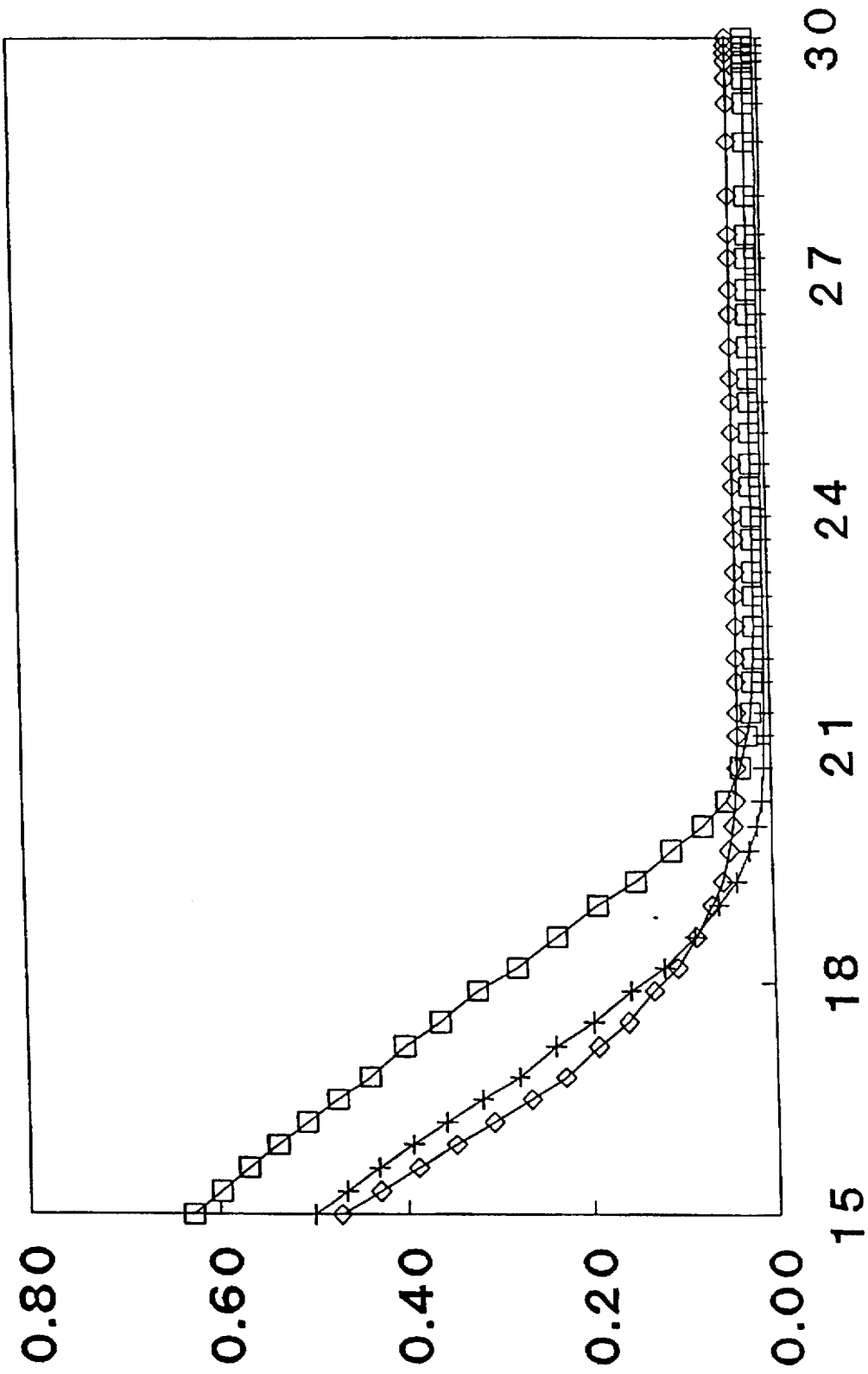
Figure 2E:
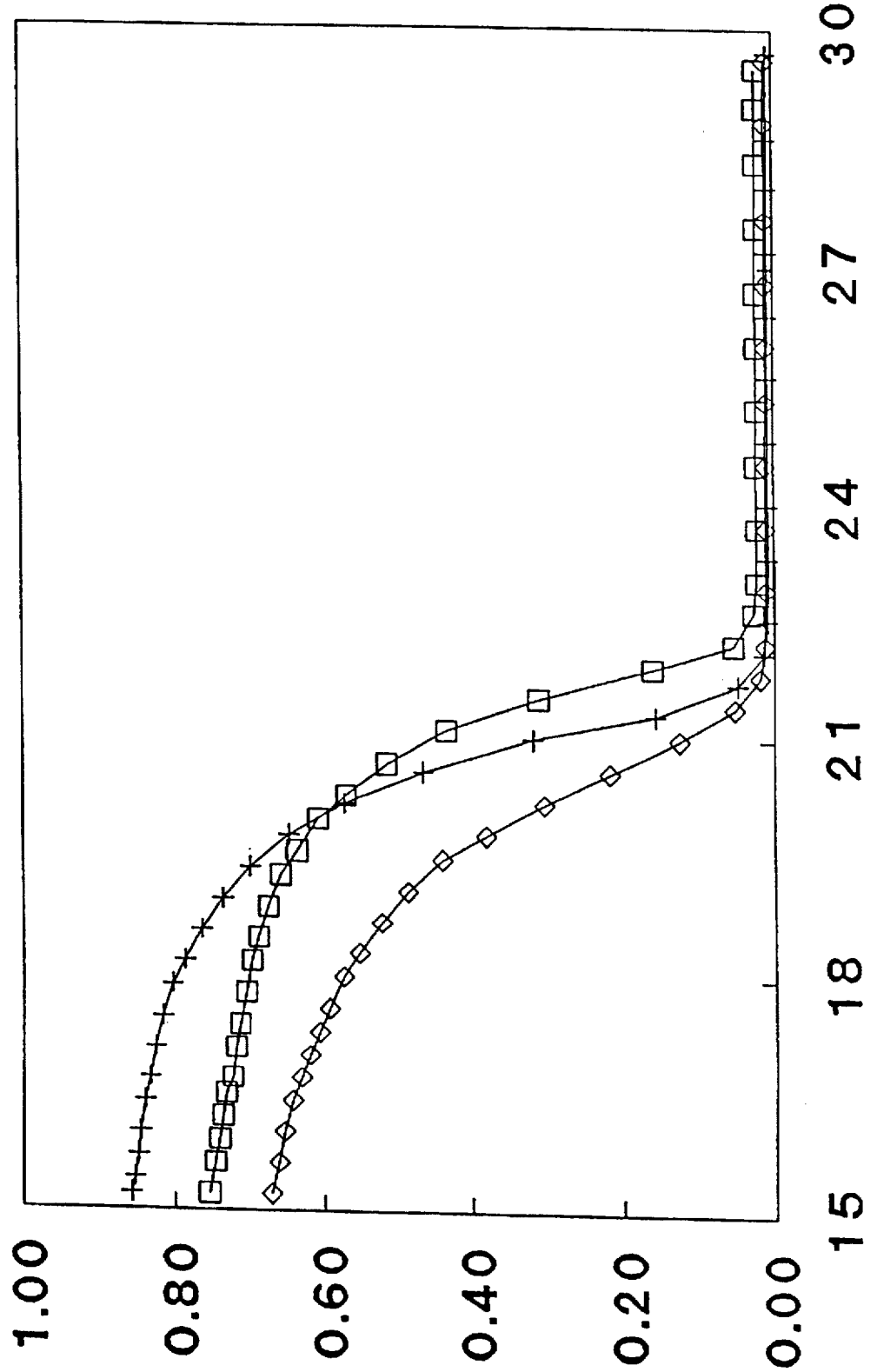
Figure 2F:
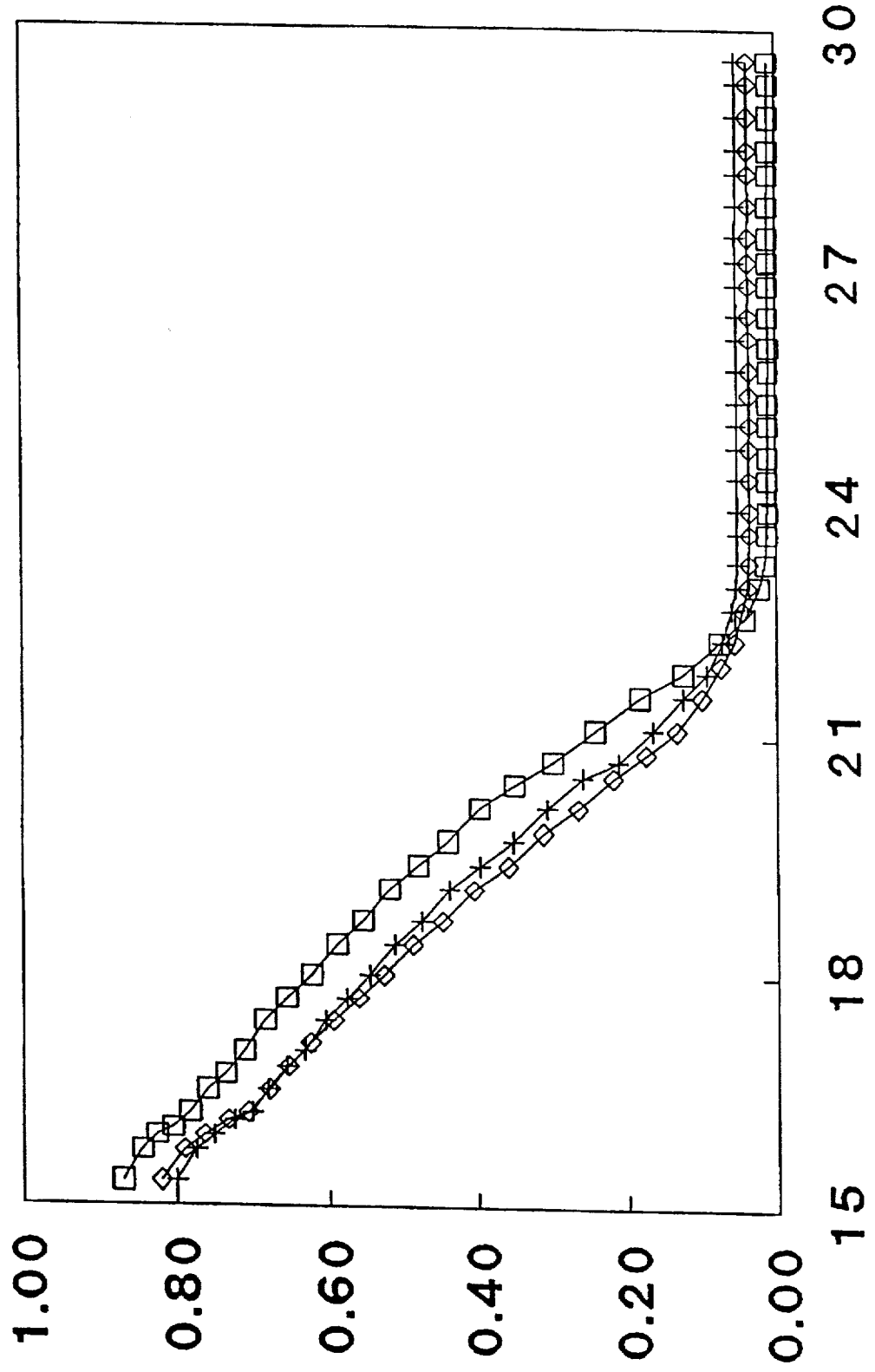

FIG. 2a corresponds to apo AI,

FIG. 2b corresponds to 18A,

FIG. 2c corresponds to M1,

FIG. 2d corresponds to M2,

FIG. 2e corresponds to M3,

FIG. 2f corresponds to M4.

Figure 3A:
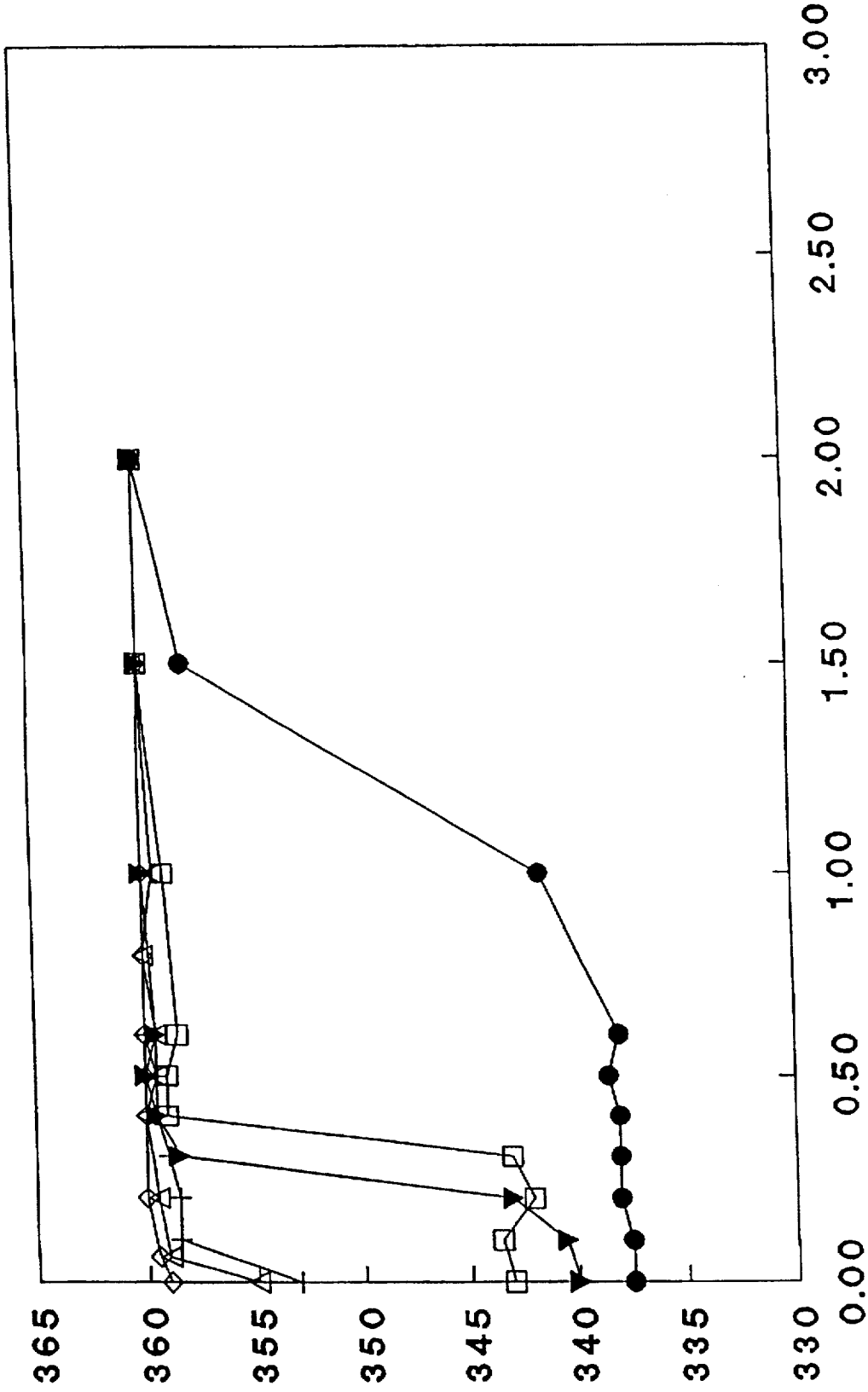
Figure 3B:
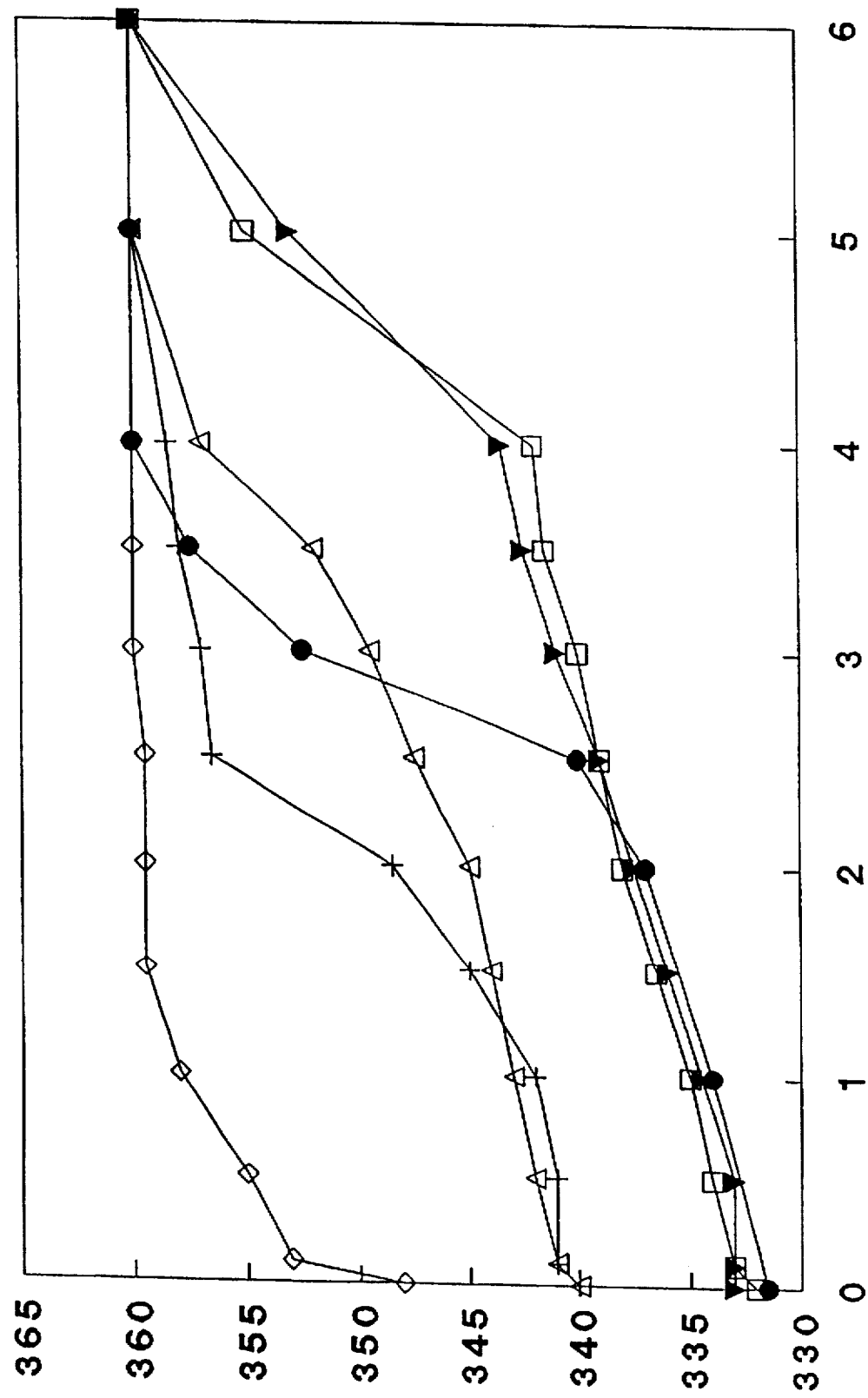

FIG. 3a and FIG. 3b represent the denaturation of the peptides and of the phospholipid-peptide complexes as a function of increasing GdmCl concentrations, by measuring the Trp maxima.

The curve with squares corresponds to M1, the curve with "+" corresponds to M2, the curve with diamonds corresponds to M3, the curve with triangles corresponds to M4, the curve with the filled circles corresponds to Apo AI, the curve with the filed triangles upside down corresponds to 18A.

The concentration of GdmCI(M) is plotted on the x-axis, and the maximal wavelength (nm) is plotted on the y-axis.

FIG. 3a corresponds to to the free peptide,

FIG. 3b corresponds to the phospholipid-peptide (DMPC) complex.

FIGS. 4a to FIG. 4f represent the gel chromatography profiles of the phospholipid-peptide complexes. Trp fluorescence intensity is measured as a function of the elution volume (expressed in ml).

Figure 4A:
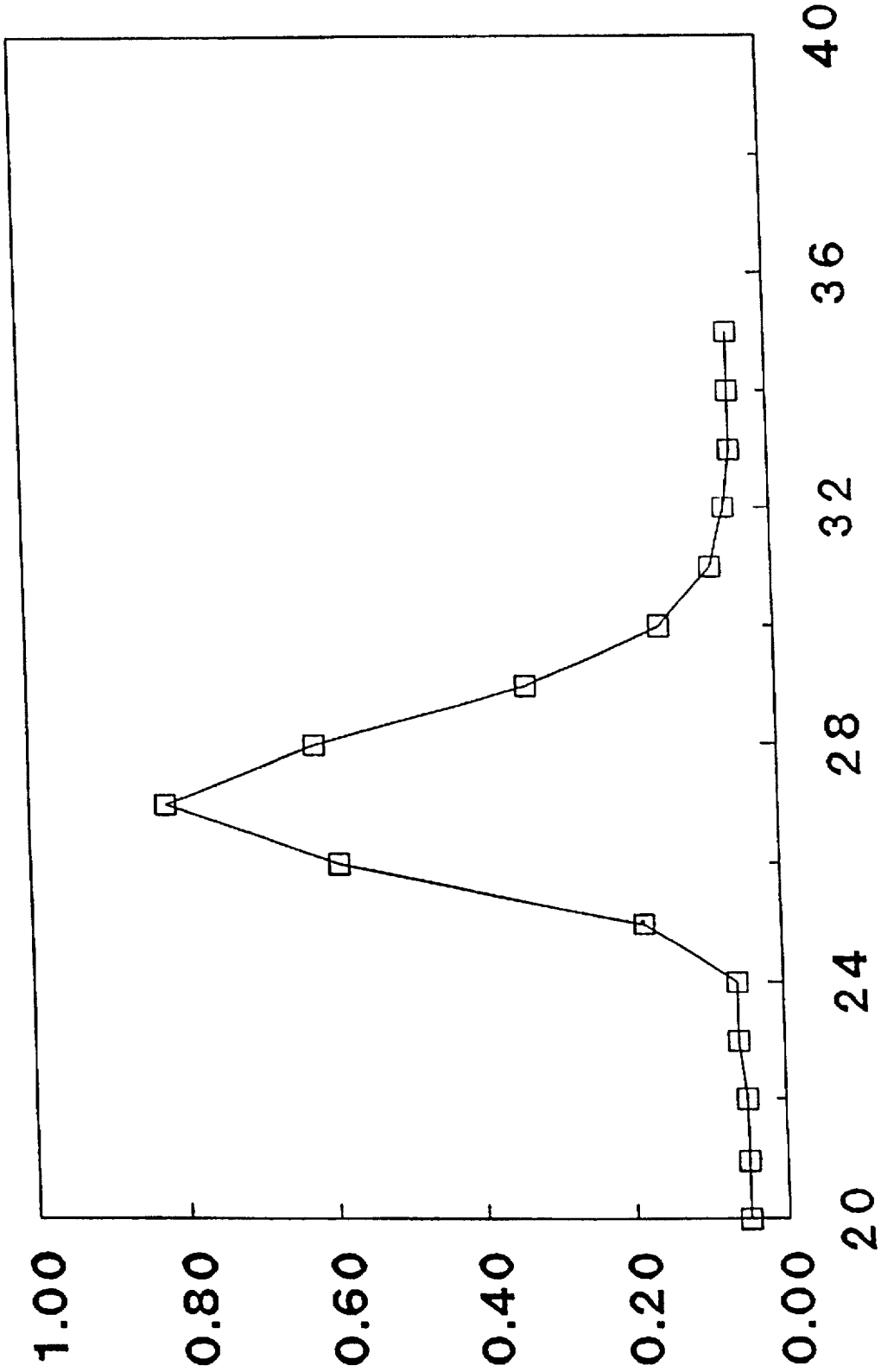
Figure 4B:
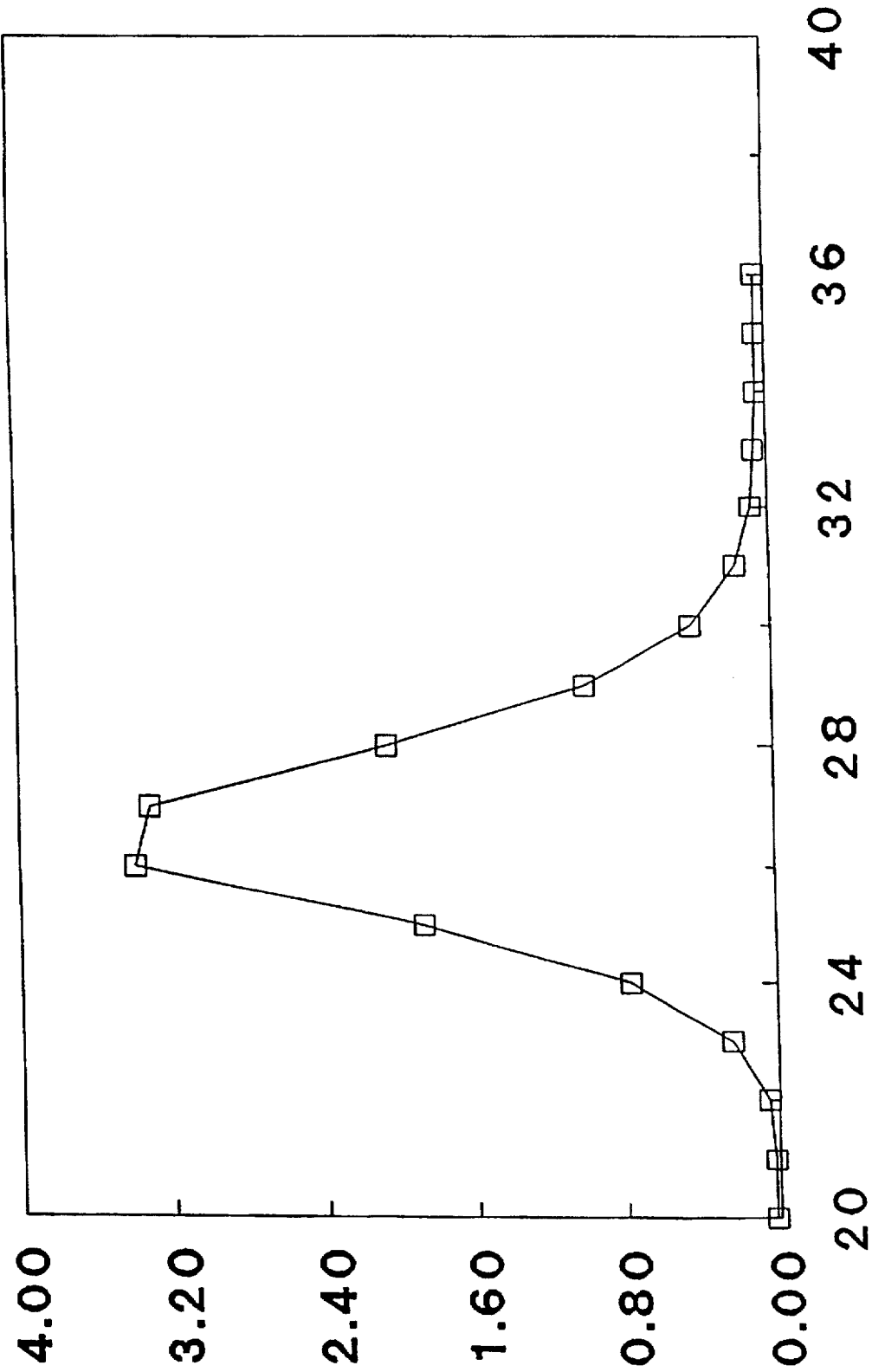
Figure 4C:
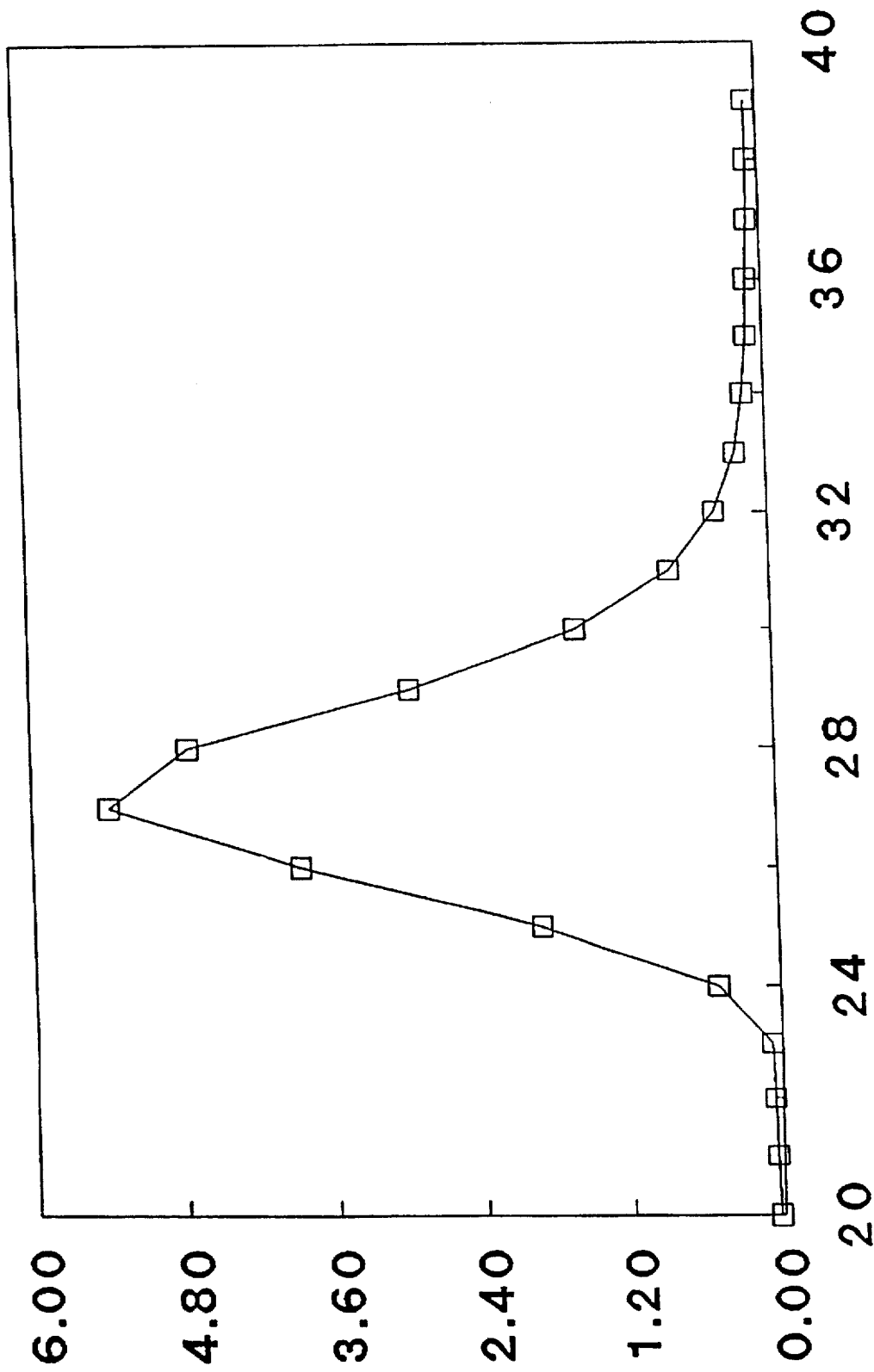
Figure 4D:
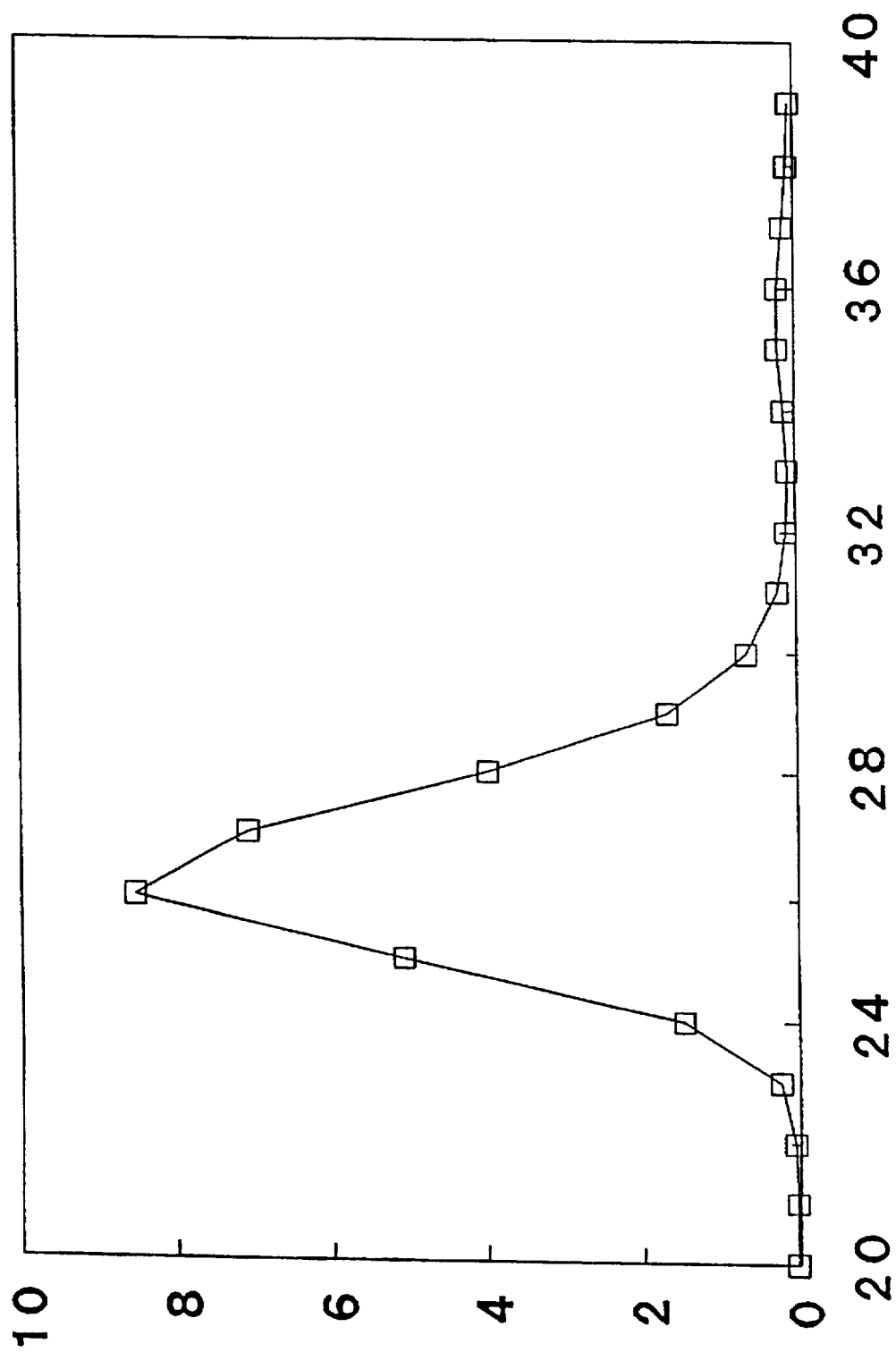
Figure 4E:
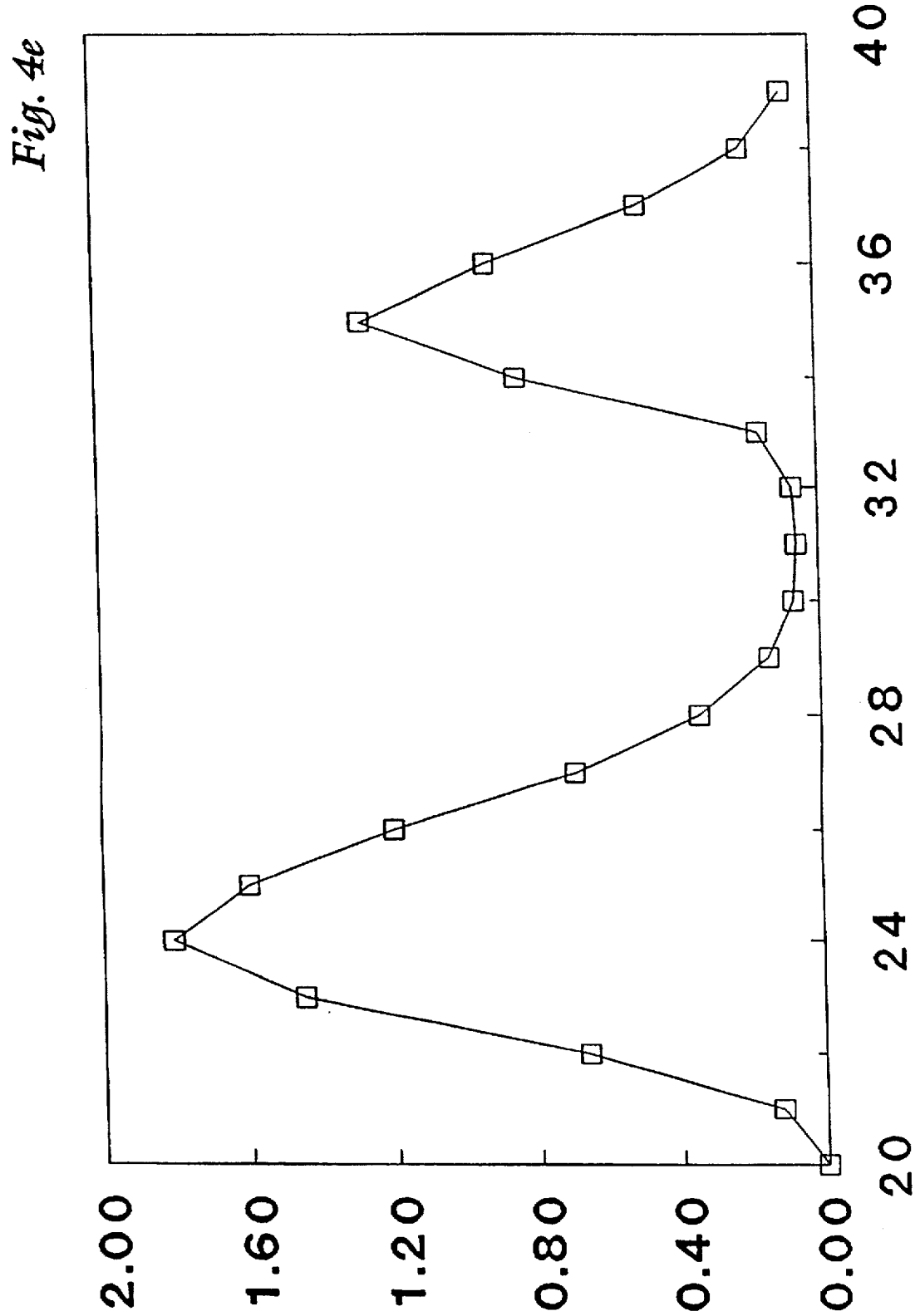
Figure 4F:
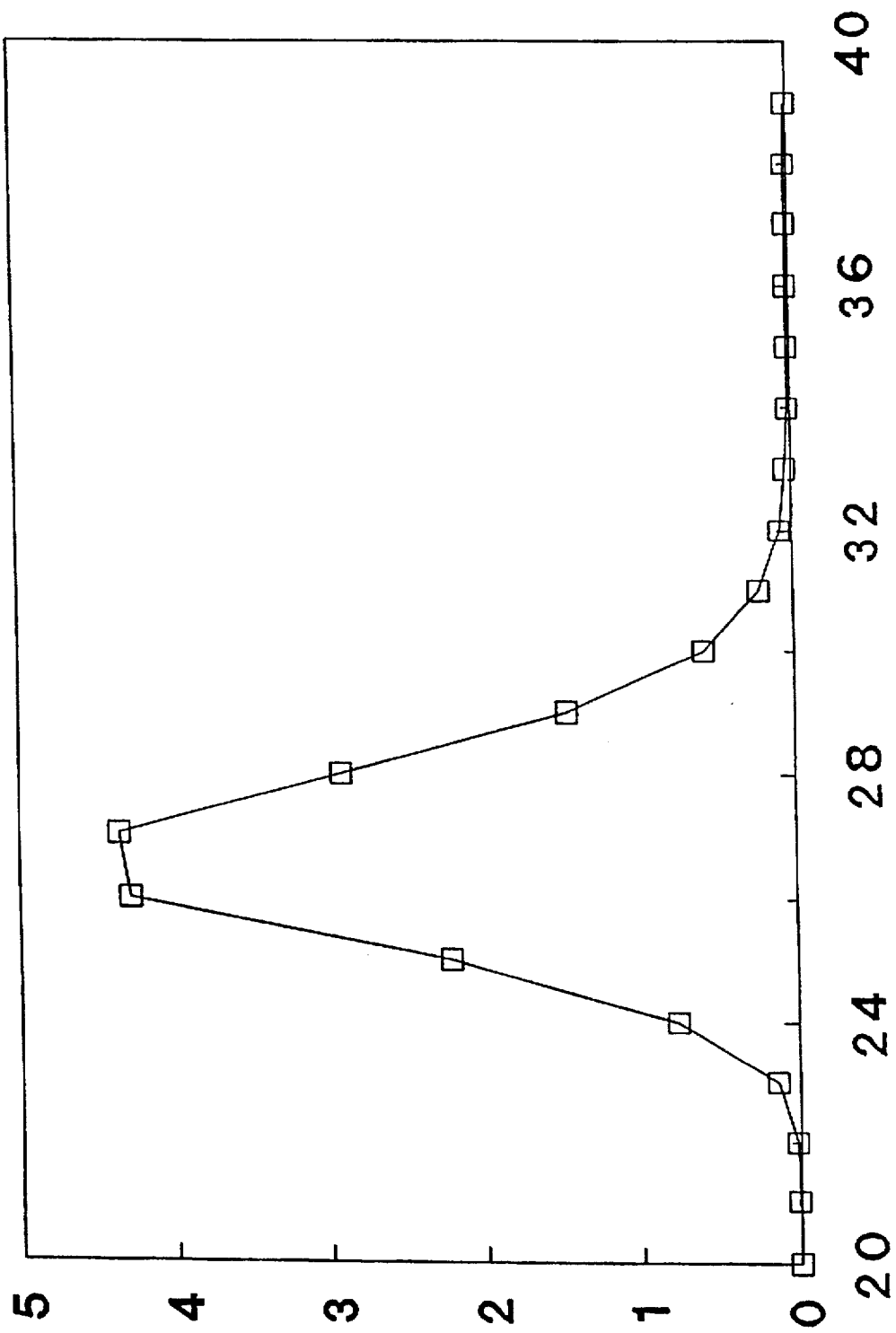

In these figures,

FIG. 4a corresponds to apo AI,

FIG. 4b corresponds to 18A,

FIG. 4c corresponds to M1,

FIG. 4d corresponds to M2,

FIG. 4e corresponds to M3,

FIG. 4e corresponds to M4.

Figure 5A:
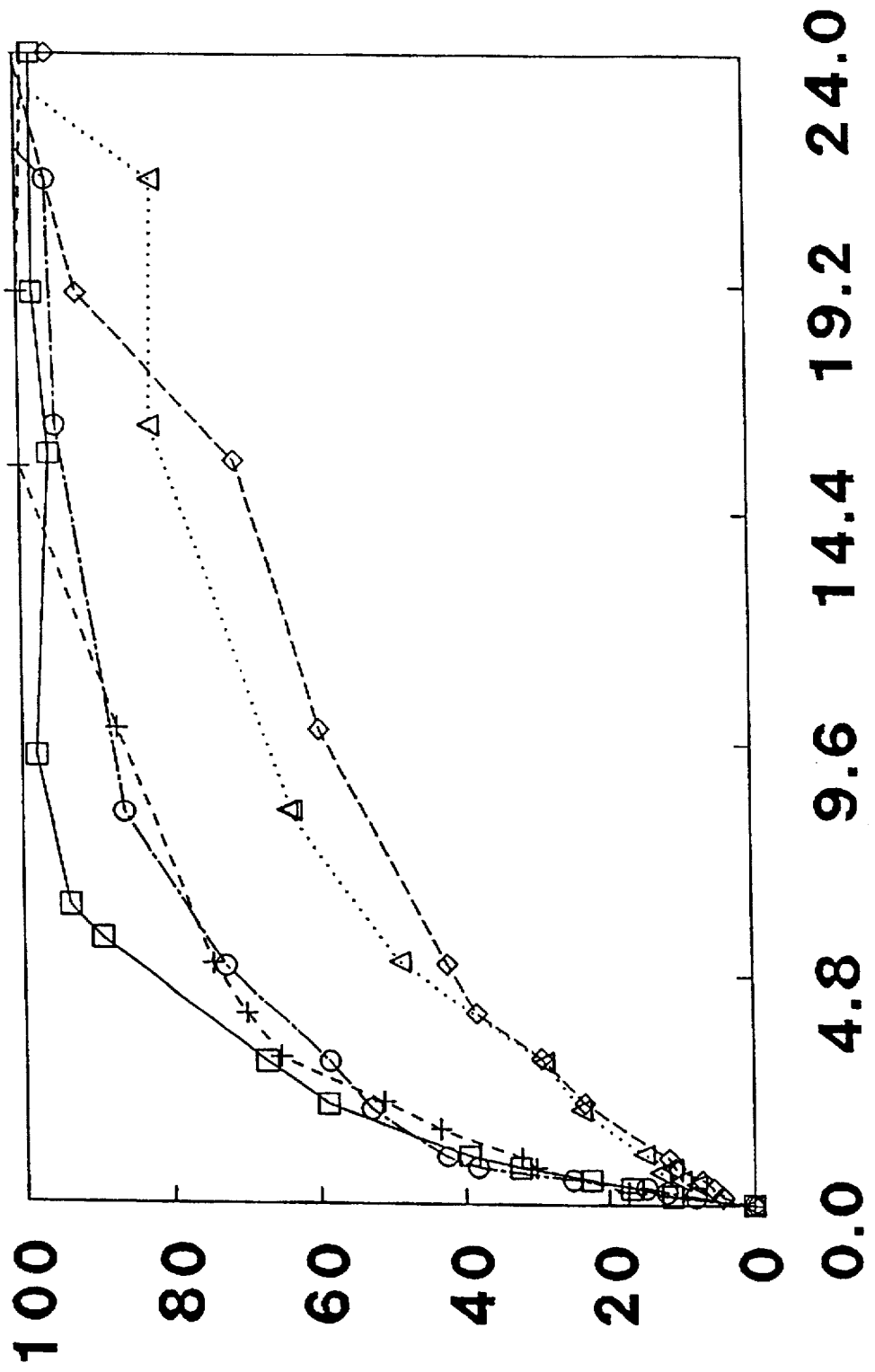
Figure 5B:
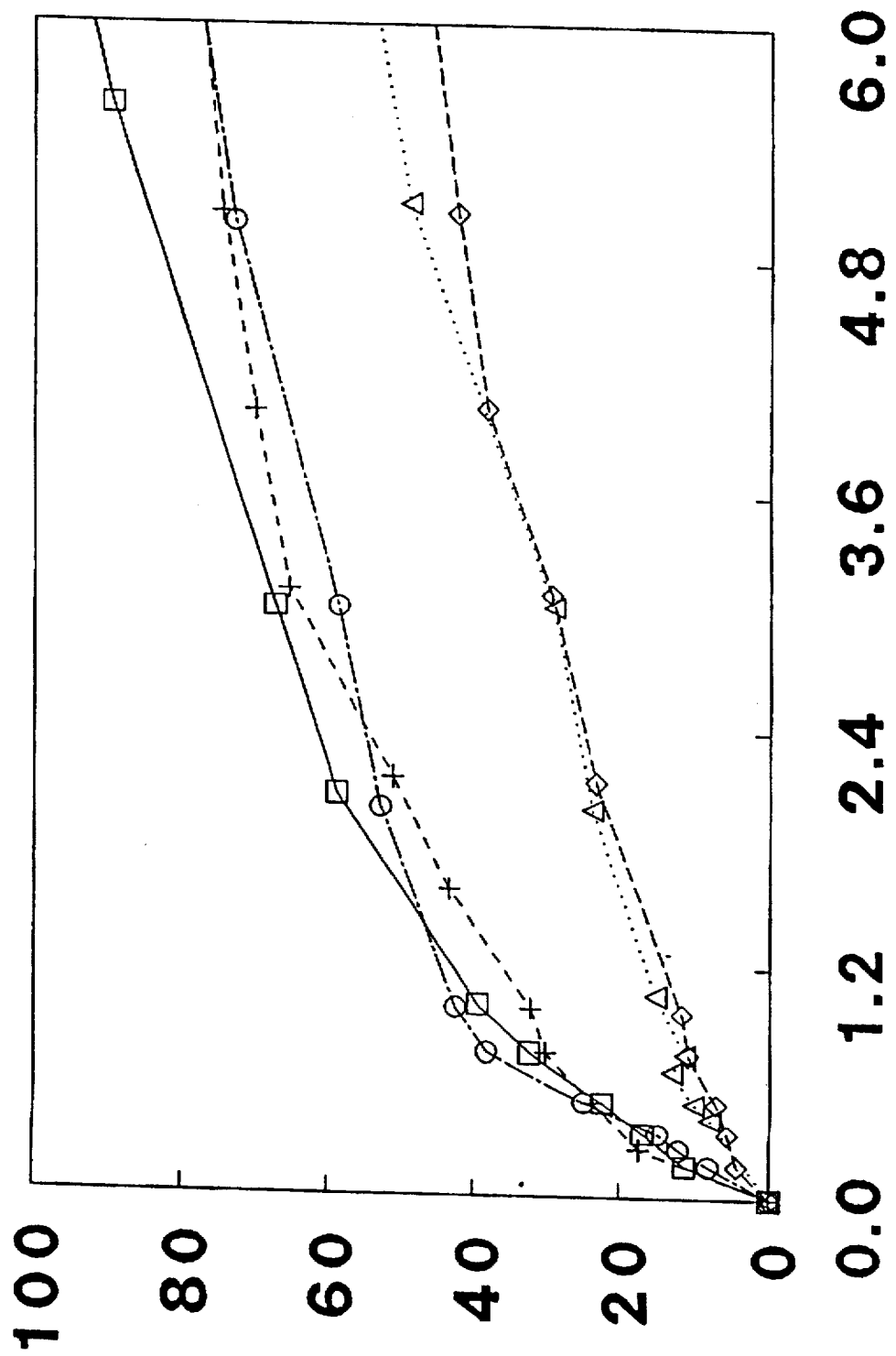

FIG. 5a and FIG. 5b represent the activation of the LCAT reaction with discoidal complexes generated between PLPC-cholesterol and different peptides or apo AI between 0 and 24 h (FIG. 5a) and between 0 and 6 h (FIG. 5b).

The time (hours) is represented on the x-axis and the % of esterification is represented on the y-axis (both figures).

The curve with "+" corresponds to M1, the curve with diamonds corresponds to M2, the curve with triangles corresponds to M3, the curve with "o" corresponds to M4, the curve with squares corresponds to 18A.

Figure 6:
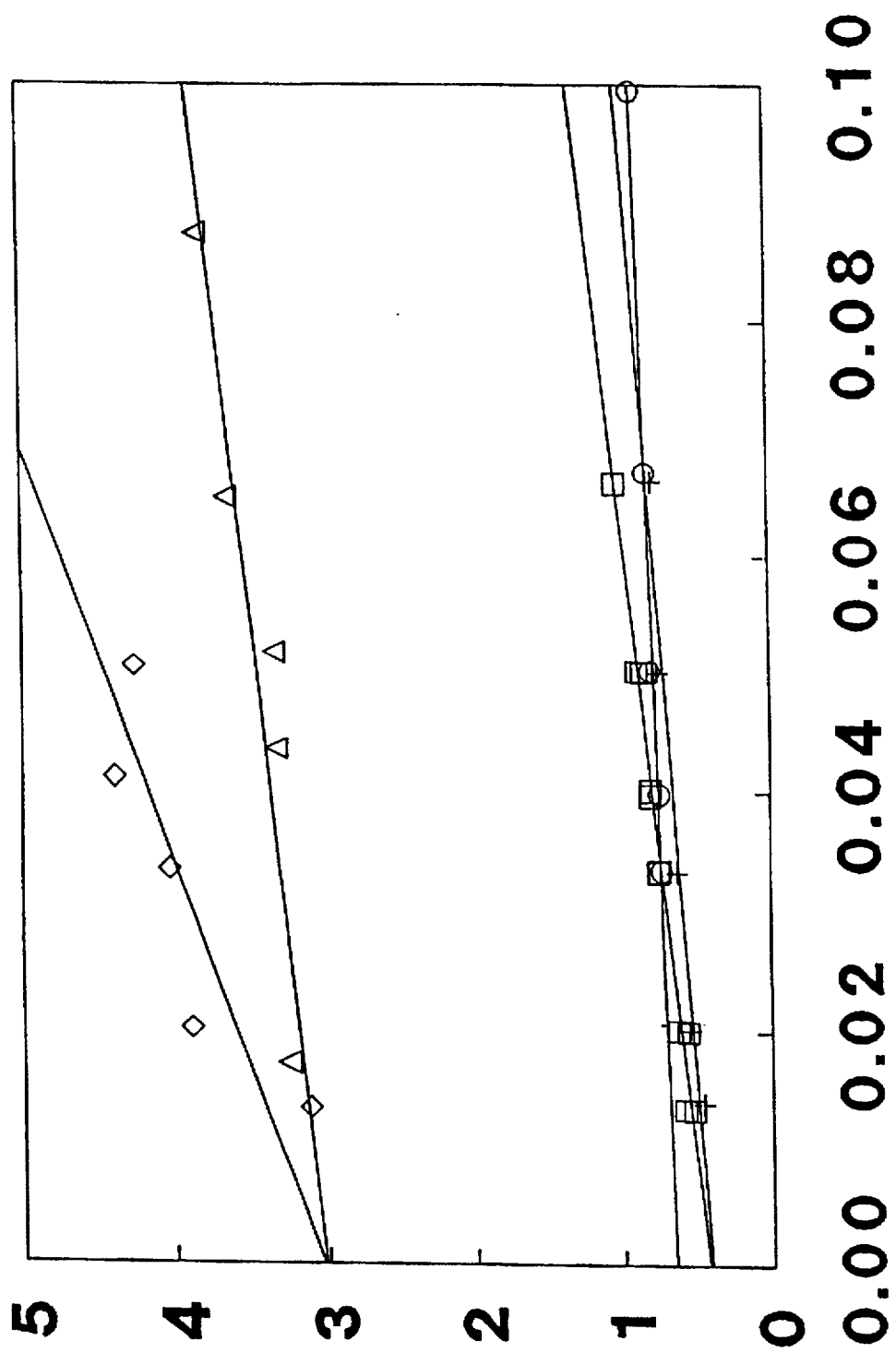

FIG. 6 represents the Lineweaver-Burk plots giving the inverse of the initial velocity (1/Vo), (on the y-axis, expressed in nmol CE/h), (CE=cholesteryl ester) as a function of the inverse of the substrate concentration (1/concentration of cholesterol expressed in µM) (on the x-axis)) for the reaction of LCAT with the different complexes.

The curve with "+" corresponds to M1, the curve with diamonds corresponds to M2, the curve with triangles corresponds to M3, the curve with "o" corresponds to M4, the curve with squares corresponds to 18A.

Figure 7:
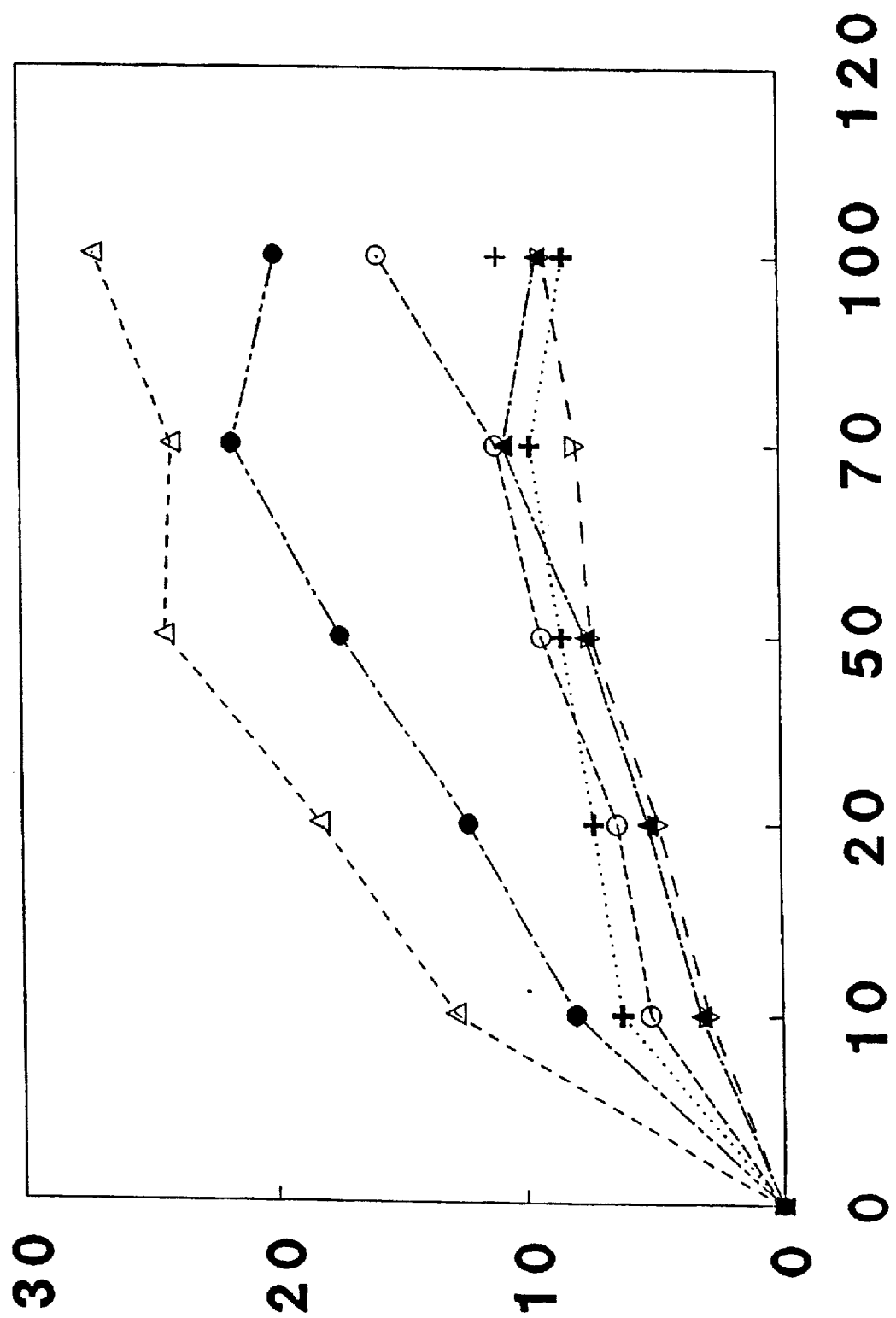
Figure 8A:
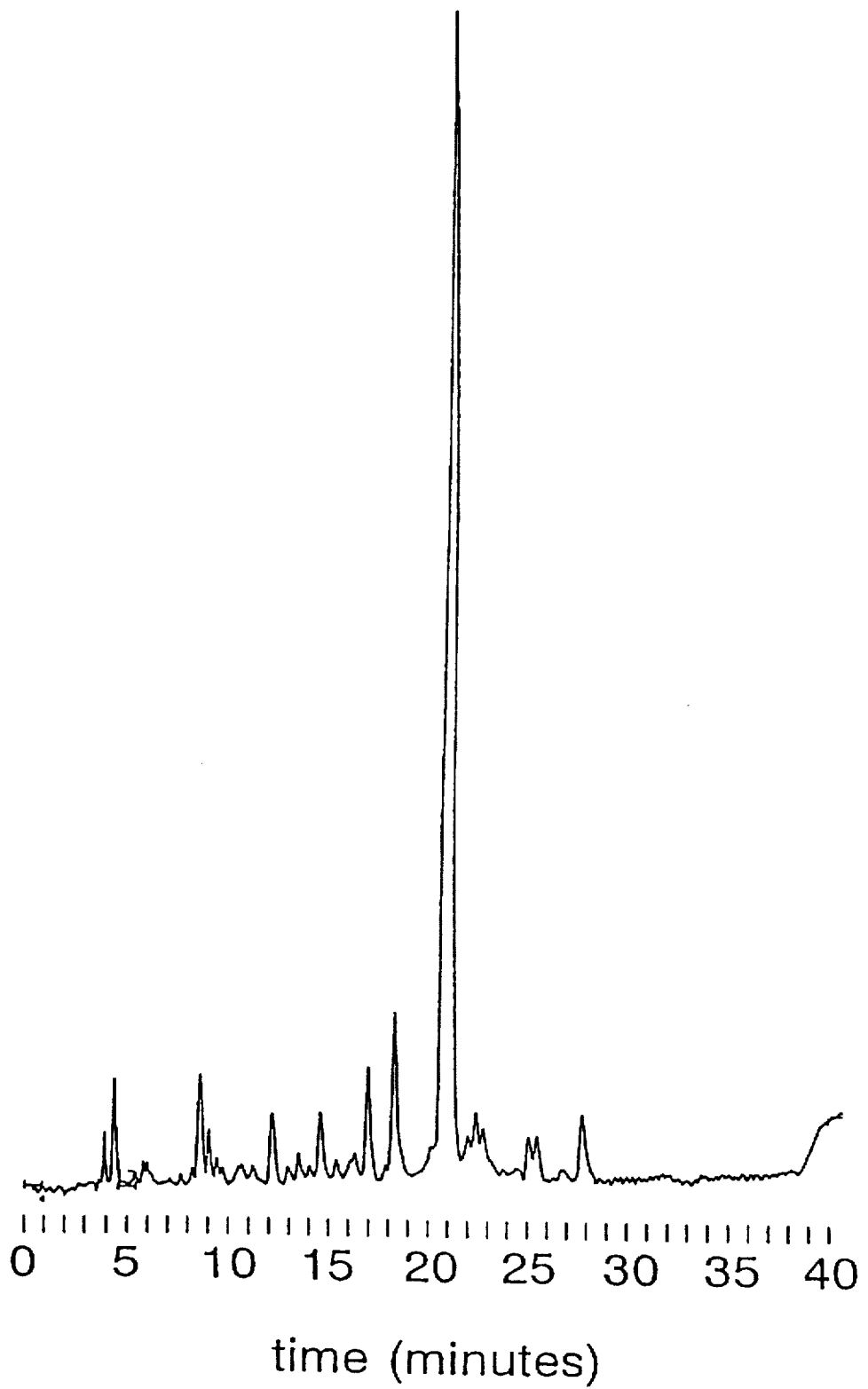
Figure 8B:
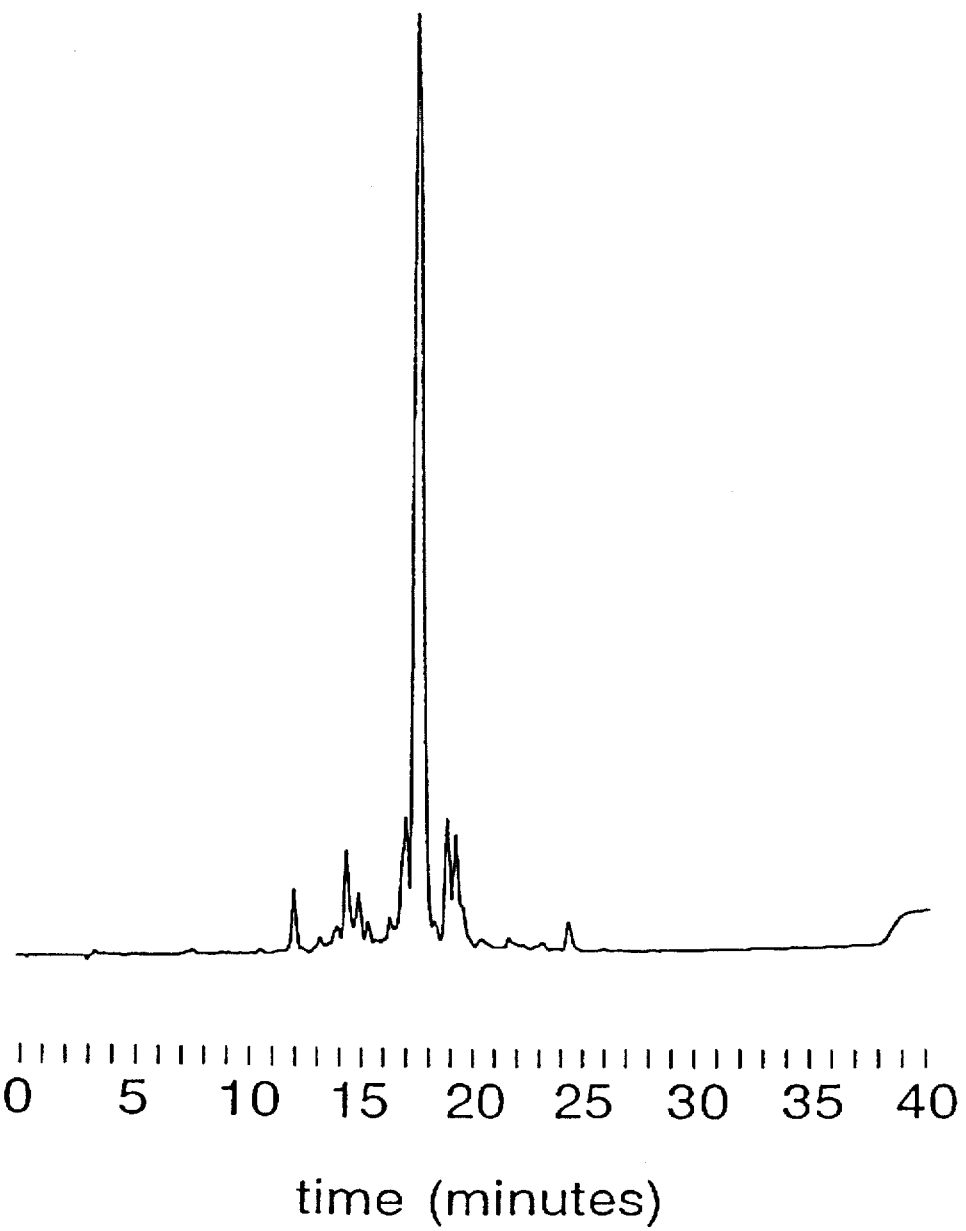
Figure 8C:
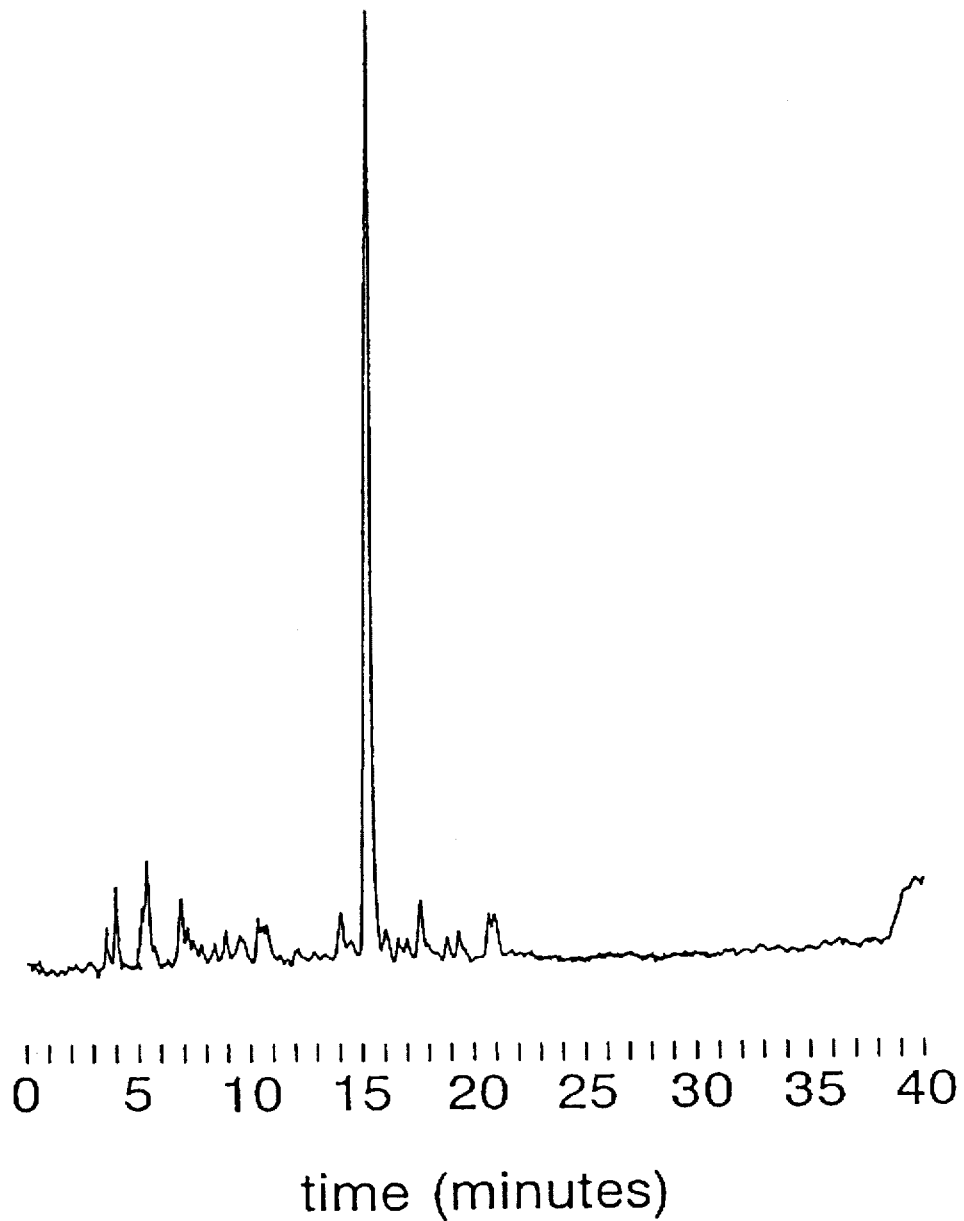
Figure 8D:
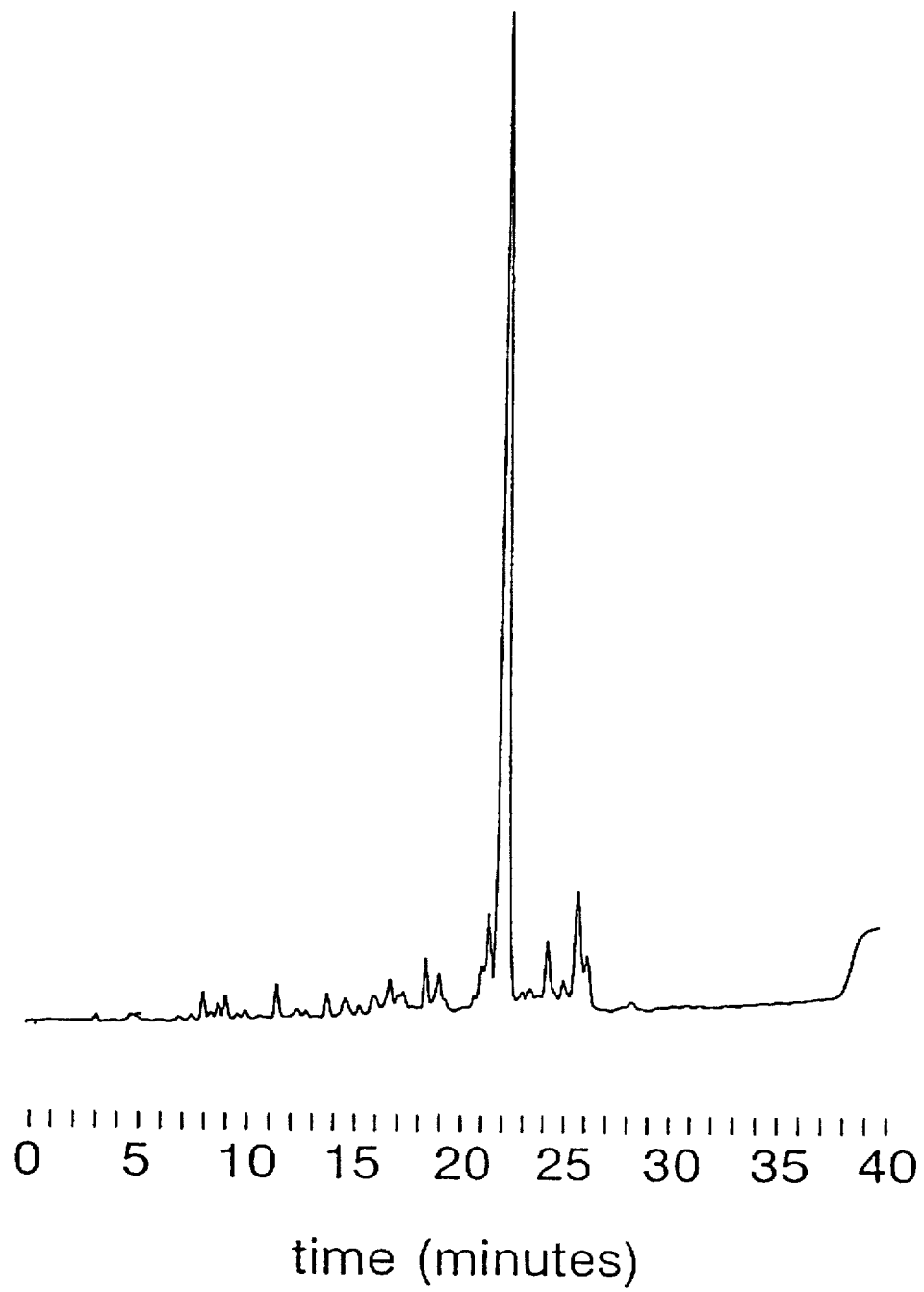
Figure 8E:
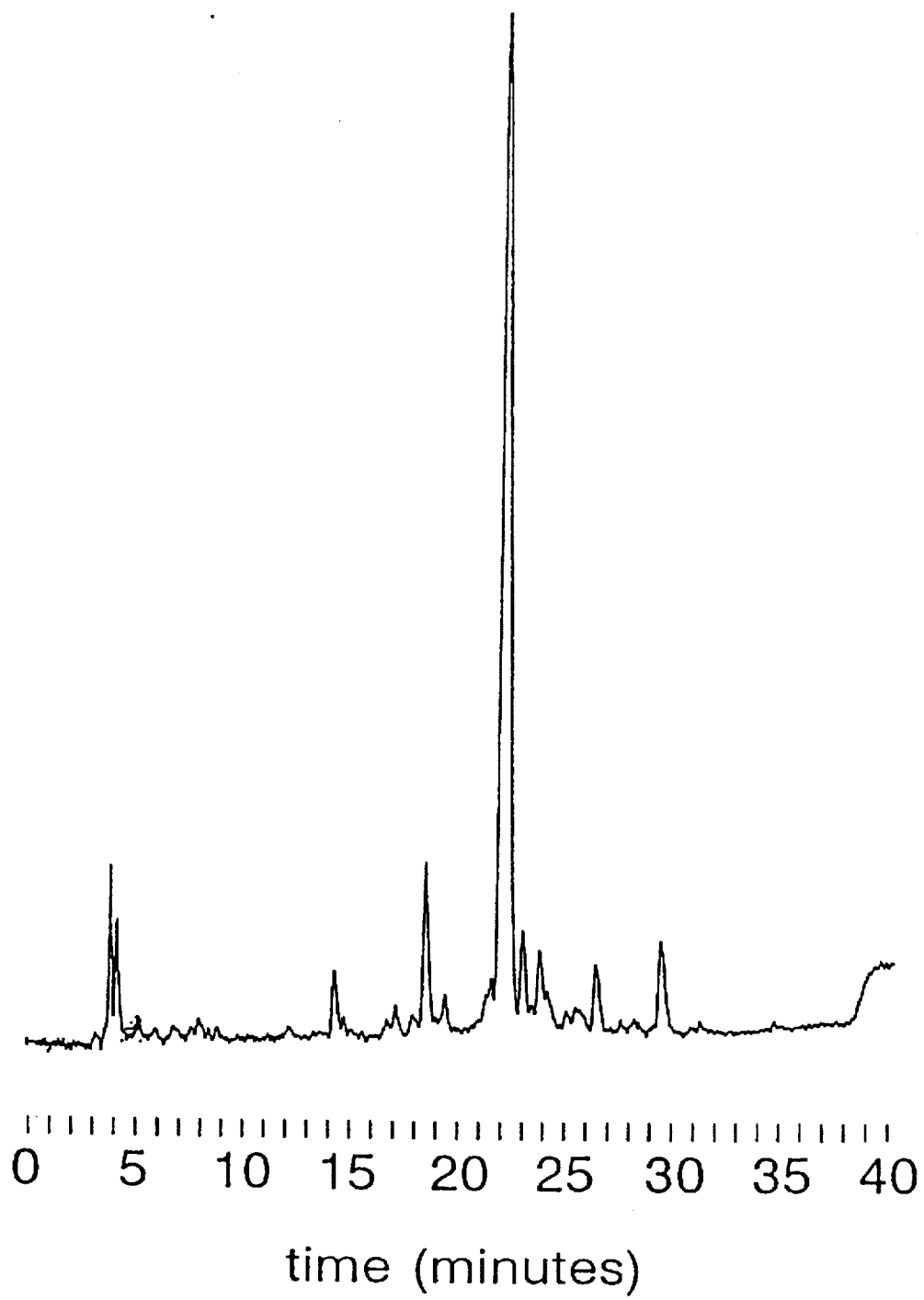

FIG. 7 represents the amount of cholesterol (µg) measured in the cell culture medium (y-axis) after incubation of the lipid-loaded macrophages (J 774 cells) with different concentrations of the peptide-phosholipid complex (x-axis, complex expressed as protein in µg/ml) of the invention. Comparisons with apoAI phosholipid and apoE-phospholipid complexes in similar condition are given.

In FIG. 7, the curve with "+" corresponds to apo AI, the curve with open triangles corresponds to 18A, the curve with the open circles corresponds to M1, the curve with the open triangles upside down corresponds to M2, the curve with the filled triangles corresponds to M3, the curve with the filled circles corresponds to M4, the curve with "—+—" corresponds to apoE.

FIG. 8 represents the reverse phase HPLC analysis of the amphipathic peptides of the invention;

panel A corresponds to peptide M1, panel B corresponds to peptide M2, panel C corresponds to peptide M3, panel D corresponds to peptide M4, panel E corresponds to peptide 18A.

The gradient specifications are the following:

0 mn to 1 mn: 30% of buffer B+70% of buffer A, 1 mn to 35 mn: 30% to 70% of buffer B (+70% to 30% of buffer A), 35 mn to 40 mn: 80% of buffer B+20% of buffer A.

Buffer A: 0.1% of trifluoroacetic acid in $H_2O$,

Buffer B: 0.1% of trifluoroacetic acid in acetonitrile.

The flow rate is 1 ml/m, the detection is carried out at a wavelength of 230 nm and the column is $C_2/C_{18}$ Pep/S reverse phase (Pharmacia).

The 18A peptide hereafter referred to is the one described by Epand et al. (1989), and has the following formula:

Glu-Trp-Leu-Lys-Ala-Phe-Tyr-Glu-Lys-Val-Leu-Glu-Lys-Leu-Lys-Glu-Leu-Phe

Table 1: corresponds to the percentage of alpha-helix structure in the free peptide and in the phospholipid-peptide (DMPC) complexes as determined by infrared spectroscopy (IR) and circular dichroism (CD).

TABLE 1

|     |     | peptide | | DMPC/peptide | |
| --- | --- | --- | --- | --- | --- |
|     |     | IR | CD | IR | CD |
| apo | AI  | 39 | 29 | 49 | 47 |
|     | 18A | 28 | 45 | 47 | 66 |
|     | M1  | 29 | 20 | 50 | 46 |
|     | M2  | 36 | 30 | 50 | 46 |
|     | M3  | 43 | —* | 61 | —* |
|     | M4  | 35 | 50 | 58 | 65 |

—* = not measured

Table 2: corresponds to the LCAT activating properties of the phospholipid-peptide complexes compared to apo AI complexes. Apparent kinetic constants are given as Vmax, Km and Vmax/Km.

TABLE 2 corresponds to the LCAT activating properties of the phospholipid-peptide complexes compared to apo AI complexes. Apparent kinetic constants are given as Vmax, Km and Vmax/Km.

| Peptide complex | Vmax nmol CE/h | Km µM FC | Vmax/Km | Vmax/Km A % of apo AI |
| --- | --- | --- | --- | --- |
| M1 | 2.41 | 14.57 | 0.17 | 15.4 |
| M2 | 0.33 | 9.40 | 0.04 | 3.3 |
| M3 | 0.33 | 2.89 | 0.11 | 10.7 |
| M4 | 1.53 | 3.83 | 0.40 | 37.3 |
| 18A | 2.32 | 21.07 | 0.11 | 10.3 |
| Apo AI° | 5.89 | 5.49 | 1.07 | 100.0 |

°Values of Vmax/Km of the apo AI and peptides can be compared since both are expressed as cholesterol-concentration (µM).
CE/h = cholesteryl esther/hour
FC = free cholesterol Table 3: corresponds to the cholesterol efflux-promoting characteristics of the phospholipid-peptide complexes compared with efflux capacities of apo AI complexes. Apparent kinetics constants are given as Vmax, Km and Vmax/Km.

TABLE 3 corresponds to the cholesterol efflux-promoting characteristics of the phospholipid-peptide complexes compared with efflux capacities of apo AI complexes. Apparent kinetics constants are given as Vmax, Km and Vmax/Km.

|     | Vmax* | Km | Vmax/Km | r* |
| --- | --- | --- | --- | --- |
| M1 | 111 | 32 | 3.5 | 0.99 |
| M2 | 48 | 7 | 6.5 | 0.98 |
| M3 | 77 | 60 | 1.3 | 0.97 |
| M4 | 50 | 10 | 5.2 | 0.99 |
| 18A | 26 | 12 | 2.1 | 0.97 |
| Apo AI° | 52 | 0.9 | 56.83 | 0.95 |

*Vmax expressed as µg cholesterol released from the cells /µg cell protein/24 hour.
**Km expressed as protein concentration of the complex in µmol/L.
***Correlation coefficient of the regression line.
°To compare apo AI versus the peptides, it should be considered that the MW of apo AI is about 10 times higher than that of the peptides.
In order to compare Vmax/Km, the value for apo AI is to be divided by 10.

Table 4: corresponds to the composition of the phospholipid-protein complexes and size measurements from the electromicrographs.

TABLE 4 corresponds to the composition of the phospholipid-protein complexes and size measurements from the electromicrographs.

| Complex with DPPC and | Composition DPPC/Protein w/w | Diameter Å MEAN ± SD |
|---|---|---|
| apo AI | 2/1 | 128 ± 22 |
| 18A | 2/1 | 155 ± 27 |
| M1 | 3/1 | 209 ± 33 |
| M2 | 2/1 | 173 ± 45 |
| M3 | 4/1 | 175 ± 55 |
| M4 | 3/1 | 150 ± 25 |

EXAMPLES

1. Peptide synthesis

The peptides were synthesized by solid-phase peptide synthesis by coupling on Tentagel S-RAM resin (Rapp Polymere, Tübingen, Germany), which is provided with the acid-labile linker 4-(α-Fmoc-amino-2',4'-dimethoxybenzyl) phenoxyacetic acid in order to obtain carboxy-terminal amides. tert-Butyl-based side chain protection and α-Fmoc-amino protection was used. In most cases coupling was carried out using preformed amino acid 0-pentafluorophenyl esters. In some cases, tryptophan was coupled using TBTU (O-1H-benzotriazol-1-yl)-N,N,N',N'-tetramethyluroniumtetrafluoroborate) activation. When this activation procedure was used, the side chain indole group of trytophan was protected with t-Boc (Novabiochem, Nottingham, UK). The amino termini of the completed peptide chains were acetylated using acetic anhydride. All syntheses were carried out on a Milligen 9050 PepSynthesizer using continuous flow procedures. Following cleavage with trifluoroacetic acid in the presence of scavengers and extraction with t-butylmethylether, all peptides were analyzed by C18 reverse phase chromatography.

2. Peptide design

This study was initiated by using the 18A peptide, described by Segrest et al., (1983), whose structural and functional properties have been extensively reported (Kanellis et al., 1980; Epand et al., 1989). When reassembled with phospholipids, this peptide generates discoidal complexes with a structure similar to that of the apolipoprotein-lipid complexes (Anantharamaiah, 1986). In such complexes, the peptide chains are adjacent to each other and oriented parallel to the phospholipid acyl chains (Brasscur, 1991). In this configuration, salt bridges can form between charged residues located on the edges of adjacent peptide chains. This effect was previously demonstrated for the helical bundle of the N-terminal segment of apo E, where salt bridges occur between charged residues occurring along the edges of the helical peptides (Wilson et al., 1991).

The hydrophobic and hydrophilic molecular potentials around the corresponding sequences, together with the angles pho and phi, were calculated using the method described previously (Brasscur, 1991).

Complex isolation and characterisation

Complexes were obtained by incubation of the peptides with dimyristoylphosphatidylcholine (DMPC, Sigma, St Louis, Mo.) vesicles at a DMPC/peptide, w/w ratio of 3/1 at 25° C. for 16 h. Complexes with dipalmitoylphosphatidylcholine (DPPC) were generated by the cholate dialysis procedure (Vanloo et al., 1991). All complexes were isolated by gel chromatography (FIG. 4) on a Superose PG column in a 0.01M Tris-HCl buffer, pH 8.0, 0.15M NaCl, 1 mM NaN$_3$, 0.1 g/L EDTA. The column was first saturated with the phospholipid to avoid dissociation of the lipid-peptide complexes. The complexes were detected by continuous monitoring of the optical density at 280 nm and by measurement of the Trp emission of the fractions on a Jasco SP500 spectrofluorimeter. The composition and size of the complexes, were determined on the two fractions with maximal UV absorption in the elution peak of the complexes. The composition was determined by quantitation of the phospholipids using an enzymatic assay (Biomerieux, France), and of the peptide by an HPLC phenylalanine assay on a C18 reversed-phase column, after hydrolysis (Vanloo et al., 1991).

Fluorescence measurements

The measurement of the Trp fluorescence emission in the peptides and in the complexes was used to monitor complex formation. The fluorescence measurements were performed on an Aminco SPF-500 spectrofluorimeter equipped with a special adapter (Aminco-J4-9501) for the fluorescence polarisation measurements. The fluorescence polarization of the lipid-peptide complexes labelled with diphenyl hexatriene (DPH) (molar ratio of 500:1 lipid:DPH) was measured as a function of the temperature to detect changes in the fluidity of the phospholipid acyl chains due to lipid-peptide association. The excitation wavelength was set at 365 nm and emission was detected at 427 nm. Temperature scans between 15° and 40° C. were performed with a circulating water bath (Julabo) at a rate of 0.6° C./min.

Electron microscopy of the lipid-peptide complexes

Phospholipid-peptide complexes, at a protein concentration of 150 µg/ml, were negatively stained with a 20 g/l solution of potassium phosphotungstate (pH 7.4). 7 µl of the samples were applied to Formvar carbon-coated grids and examined in a Zeiss EM 10C transmission electron microscope operating at 60 kV. Particle size was determined by measuring 120 discrete particles for each sample. The mean diameter and the size distribution of the complexes were calculated.

Infrared spectroscopy measurements (Table 1)

Attenuated Total Reflection (ATR) infrared spectroscopy was used for the determination of the relative orientation of the apolipoprotein alpha-helical segments and of the phospholipid acyl chains as previously described for apo AI and apo AI-phospholipid complexes and for LDL (Vanloo et at., 1991). For these measurements, a 70 µL solution of 20 µg isolated complex in a 0.005M Tris-HCl buffer pH 8.4, was spread on a ATR Germanium crystal plate. Deuteration of the sample was performed by flushing N$_2$, saturated with D$_2$O, in a sealed universal Perkin-Elmer sample holder, at room temperature for 3 hours, in order to avoid overlapping of the absorption bands for random and alpha-helical structures.

Spectra were recorded on a Perkin Elmer 1720X infrared spectrophotometer, using polarized incident light with a perpendicular (90°) and parallel (0°) orientation. A dichroic spectrum was obtained by substracting the spectrum recorded with polarized light at 0° from that at 90°. A positive deviation on the dichroic spectrum indicates a dipole preferentially oriented close to a normal to the plane, while a larger absorbance at 0° is indicative of a dipole oriented close to the Ge crystal plane. The angle between a normal to the Ge crystal and the dipole is obtained from the calculation of the dichroic ratio $R_{arr}=A(90°)/A(0°)$, representing the ratio of the absorbances on the spectra recorded with polarized light at 90° and 0° . For each experiment, up to 15 scans were stored and averaged.

Circular dichroism measurements (Table 1)

Circular dichroism spectra of the peptides and their complexes with lipids were measured on a Jasco 600 spectropolarimeter at 23° C. (Brasscur et at., 1991). Measurements were carried out at a protein concentration of 0.1 mg/ml in a 0.01M sodium phosphate buffer pH 7.4. Nine spectra were collected and averaged for each sample. The secondary structure was estimated according to the generalized inverse method of Compton and Johnson (Compton et at., 1986).

Denaturation experiments

The stability of the DMPC-peptide complexes, was compared by following the maximal emission wavelength of the Trp residues after exposure to increasing quantities of GdmCl. For these experiments aliquots of a 8M GdmCl solution were added to the complex in the Tris-HCl buffer described above (see FIG. 3).

LCAT activation properties of the complexes (see FIG. 5 and 6, Table 2)

The activity of the LCAT enzyme with the various peptide-lipid complexes as substrates was determined by measuring the mount of cholesteryl esters generated during the enzymatic reaction by HPLC (Vercaemst et al., 1989).

The assay mixture consisted of variable mounts of complexes at cholesterol concentrations varying between 5 and 100 µM, 5 mg defatted bovine serum albumin (Sigma), 6 mM beta-mercaptoethanol in a reaction volume of 0.2 ml. After a preincubation of 20 min at 37° C., the enzymatic reaction was initiated by adding 3–6 µl of the semi-purified LCAT enzyme. The reaction was followed at 37° C. and was stopped by extraction of the incubation mixture with hexane-isopropanol 3:2, v/v. The solvent mixture contained either cholesteryl heptadecanoate (Sigma) or beta-sitosterol (Sigma) as internal standards for respectively cholesteryl esters and unesterified cholesterol quantification.

The unesterified cholesterol and the cholesteryl esters are identified and quantified by isocratic HPLC on a reversed-phase Zorbax ODS column, eluted with acetonitrile-isopropanol at a ratio of 90:10 v/v for unesterified cholesterol and of 50:50 v/v for cholesteryl esters. Detection was performed by measuring the UV absorbance at 205–210 nm. At a column temperature of 50° C. and with a flow-rate of 1.2 ml/min, the separation is completed within 25 min (Vercaemst et al., 1989). The sensitivity of this HPLC technique is similar to that of the conventional radioactive assay for polyunsaturated lecithin substrates (50 ng), and is about twice as low for saturated lecithins (80 ng).

The time course of cholesterol esterification by the LCAT enzyme with discoidal substrates consisting of PLPC, cholesterol, and the synthetic peptides, was followed between 0 and 24 h (Jonas, 1987). For the determination of the kinetic parameters, the initial velocities were determined in the linear portion of the curves, i.e. between 0–30% cholesteryl esters formation. The sample concentrations were in the range of $5 \times 10^{-7}$ to $5 \times 10^{-6}$ M with a constant enzyme volume of 5 µl, so that a linear production of cholesteryl esters formation was measured within 10 min at 37° C.

The initial kinetics (Vo) as a function of the apoprotein or peptide (C) concentrations were analyzed using a Lineweaver-Burk plot of 1/Vo versus 1/C. Linear regression analysis yielded the apparent kinetic parameters: Vmax, Km and Vmax/Km for each apoprotein or peptide-lipid complex. All kinetic experiments were performed at least three times and Vmax and Km values were expressed as mean ±error on the intercept and slope of the regression line.

Cellular cholesterol efflux (FIG. 7, Table 3)

J774 murine macrophages are grown in DMEM (Gibco) with addition of 10% fetal calf serum (FCS), in a 5% $CO_2$ atmosphere. Cells are seeded in 35 mm dishes at a density of $2 \times 10^6$/dish, grown for 18 h in 2ml DMEM-10% FCS and used as confluent monolayers. After 18 h, the cells are washed twice with DMEM and incubated with acetylated LDL at a concentration of 100 µg apo B/ml for 24 h in a medium consisting of DMEM and 10% lipoprotein deficient serum (LPDS). LPDS is prepared from fetal cell serum (Gibco) by eliminating all lipoproteins by ultracentrifugation. After loading with cholesteryl esters, cell monolayers are washed with DMEM.

The cholesteryl ester-laden cells are incubated in 2 ml DMEM supplemented with 1 g/l bovine serum albumin and containing the Sandoz 58-035 compound at a concentration of 1 µg/ml medium as inhibitor of the acyl-CoA:cholesterol acyl transferase enzyme (ACAT) in order to prevent the re-esterification of the cellular cholesterol (Brown et at., 1980). The cholesterol acceptors, i.e. the discoidal peptide-lecithin complexes were added to the medium at concentrations varying between 10 and 200 µg peptide/ml and cells were incubated for 24 h.

After incubation, cells are washed once with phosphate buffer pH 7.4, 0.15N NaGl (PBS) containing 2 g/l BSA and twice with PBS alone. Lipid extracts are prepared by addition to the cell pellet of 5 ml hexane/isopropylalcohol (3:2) (Phillips et at., 1987). Fifty µl of a cholesteryl heptadecanoate solution in chloroform at a concentration of 500 µg/ml are added as internal standard for the HPLC quantitation of cholesteryl esters. After vortex-mixing for 3 min and centrifugation at 3000 rpm for 15 rain, the organic phase supernatant is dried, the precipitate is dissolved in 1 ml chloroform and washed three times. The dry residue is finally dissolved in 50 µl of a mixture of chloroform:acetonitrile:isopropylalcohol (1:1:1), of which 20 µl are injected into the HPLC system.

The same extraction procedure is applied to 1 ml of the medium. For quantification of the unesterified cholesterol fraction, beta-sitosterol is used as internal standard according to methods known in the art.

After delipidation, cellular proteins were dissolved in 0.1M NaOH and the proteins were assayed either by the method of Lowry (Lowry et al., 1951) or with the bicinchoninic acid (BCA) reagent using a kit for protein assay manufactured by Pierce (Pierce Europe, oud-Beijerland, Holland). In both cases bovine serum albumin was used as a standard.

It is to be noted that 18A referred to in the Examples is the 18A derived peptide as described by Epand et al. (1989), and the formula of which has already been stated hereabove.

RESULTS

Peptide isolation

The HPLC purification patterns of the three peptides on a reverse-phase column are shown in FIG. 8. The above-mentioned 18A4-derived peptide is the most hydrophobic since the K8-E substitution in the M1 peptide and especially the F6-E substitution in the M2 peptide both increase the hydrophilicity of the peptides. The major peak corresponded to 90% of the synthetized material.

The properties of the peptide of the invention are compared with those of the prior art peptide constituted by the 18A derived peptide as described by Epand et al. (1989). The latter peptide is referred to in the Examples, in the figures and in the tables as "18A".

Reassembly of the peptides with phospholipids

The formation of small discoidal particles between DMPC vesicles and the peptides was monitored by measuring the turbidity decrease at 325 nm as a function of temperature. FIG. 1 shows that a scan through the transition temperature of DMPC decreases the turbidity of the mixtures prepared with the peptides. The turbidity decrease initiated by the peptide-lipid association started already at 17° C., below the DMPC transition temperature and stabilized around 23° C. The turbidity decrease enables to determine the binding affinity of lipids to the peptides of the invention. M 1 has a strong lipid binding capacity while 18A and M4 have quite similar lipid binding affinity. The lipid binding of M3 is low compared with the other peptides.

Complex formation was further monitored by measuring the Trp fluorescence emission spectrum (see FIG. 2). The maximal emission wavelength for the M1 and M2 peptides lies at 341 and 353 nm, respectively (FIG. 3). The maximal emission wavelength at 353 nm of the M2 peptide is indicative of an exposed conformation of the Trp to the solvent. A blue shift to 335 and 342 nm was observed upon phospholipid binding of the M1 and M2 peptides due to the more hydrophobic environment of the Trp in the complexes (FIG. 3). In apo AI, the Trp emission wavelength was shifted from 333 to 329 nm only, suggesting that the Trp residues are in a more hydrophobic environment in the native protein than in the synthetic model peptides (Anantharamaiah, 1986).

Complex formation was monitored by measuring the degree of fluorescence polarization after labelling with DPH. A decrease of the fluorescence polarisation, indicative of a decreased mobility of the phospholipid acyl chains, was observed between 25° and 55° C. corresponding to the crystalline to liquid crystalline transition of the DPPC acyl chains. In all the phospholipid-peptide mixtures, the transition temperature of DPPC was shifted towards high temperatures compared to that of the pure phospholipid.

Separation and characterization of the DPPC-peptide complexes

The lipid-protein complexes generated between apo AI, the synthetic peptides and DPPC, at a 3/1, lipid/protein, w/w ratio, were fractionated on a Superose PG column (FIG. 4). When the complexes were prepared with DPPC using the cholate dialysis procedure, the mixtures were more homogenous (FIG. 4). They eluted as a symmetrical peak at an elution volume comparable to that of the DPPC-apo AI complexes. For the M3 complex, the complex size is much larger and a peak of free peptide can be observed.

The composition of the complex, corresponding to the maxima of the elution peak of the complex in the chromatographic elution patterns (FIG. 6) is summarized in Table 4. Added to this table are the diameters of the complexes obtained by electron microscopy. The diameter and distribution of the particles were determined by measurement of the electron micrographs.

Generally DPPC-peptide complexes have a diameter ranging from about 150 Å to about 200 Å, with M4 presenting the smallest diameter. 18A and M4 complexes have similar sizes, while M1, M3 and M2 complexes are larger. All the diameters for the peptide-phospholipid complexes are larger than the diameters observed for DPPC-apo AI complexes.

Stability of the complexes

Denaturation experiments monitoring Trp emission were performed with apo AI and with the three peptides since they contain a Trp residue at position 2. These experiments, performed by titration with increasing GdmCl concentrations, show that the exposure of the Trp residues in apo AI and in the peptides increases with the GdmCl concentration (FIG. 3). As shown on FIG. 3, the Trp is more exposed to the solvent in the M2 peptide than in the other peptides and in apo AI as the Trp maximal wavelength lies at 353 compared to 338 nm in apo AI. The midpoint of the transition lies around 0.3M for the M1 peptide and at 0.25M for the 18A, as compared with 1.3M for apo AI. The transition occurs immediately after the addition of GdmCl to the M2. For the M3 and M4 peptide, this occurs at a concentration around 0.1M (FIG. 3). For the M4 this can be explained by the Trp in position two that is more exposed to the aqueous solvent and more accesible for denaturation.

The association with lipids (FIG. 3 lower part) stabilizes the protein structure and protects it against denaturation, as the Trp emission shifts towards lower wavelengths in the complexes and the midpoint of the denaturation increases up to 4, 3 and 2.5M for the M1, M2 and the M4 phospholipid complexes respectively and to 2.5 for the apo AI phospholipid complex. For the M3 phospholipid-peptide complex, the denaturation occurs immediately.

Determination of the helical content and of the orientation of the helices in the complexes The secondary structure of the peptides and of the peptide-lipid complexes was obtained by CD measurements (Table 3). As previously observed for apo AI (Brasseur, 1991; Vanloo et al., 1991) the binding to phospholipids increased the alpha-helical content of the peptides by 20% while decreasing the random coil content. The percentage of alpha-helical structure was further determined by ATR infrared spectroscopy and the results from the two techniques are compared in Table 4. Compared to the IR measurements, the CD data tend to underestimate the alpha-helical contribution of the peptide-lipid complexes and to overestimate the percentage of random structure and beta turns (Table 4) as observed for the apo AI-DMPC complex and for LDL (Goormaghtigh et at., 1989; Brasscur, 1991). This might be due to differences in the method of analysis and the curvefitting procedures used in the two techniques (Goormaghtigh et al., 1989).

In order to determine the orientation of the alpha-helices with respect to the DMPC bilayer, ATR infrared spectra of DMPC and of the isolated peptide-DMPC complexes were recorded at two orthogonal linear polarizations of the incident light. In the peptide-DMPC complexes, the dichroic ratio for the acyl chains indicates that the hydrocarbon chains are tilted at an angle of 24° from the axis perpendicular to the Ge surface. This value is close to that measured for the apo AI-DMPC complex (Vanloo et al.,1991), and higher than that for pure DMPC. For the M1, M2, M3 and M4 peptide-DMPC complexes, the corresponding angles between the peptide and an axis perpendicular to the Ge plane are respectively 25°, 25°, 34° and 31°. From these data, it can therefore be assumed that the helical peptides and the phospholipid acyl chains are oriented parallel to one another.

LCAT activation kinetics with various substrates.

The kinetics of the reaction of the semi-purified LCAT enzyme with discoidal complexes generated between the peptides, PLPC and cholesterol as substrate were followed between 0 and 24 h, and compared with those of the apo AI/PLPC/cholesterol complexes. The expression "semi-purified" corresponds to the concentration relative to that in plasma by a factor of 5100, with the major contaminant being albumin. The time course of the reaction, expressed as the percentage of esterified cholesterol as compared with the original substrate is shown on FIGS. 5a, 5b and 6 and in Table 2. These figures demonstrate that, using discoidal complexes as substrates, the fastest kinetics are observed with substrates containing apo AI (data not shown in figures but is Table 2). The M1, M4 and 18A phospholipid-peptide complexes give the fastest kinetics, while for the complexes formed with M2 or M3 peptide, a low rate of cholesterol esterification was observed during the first hour of the reaction. For all substrates, saturable kinetics were observed, as a plateau was reached at times varying between 2–4 h for substrates containing apo AI (data not shown), and up to 24 h for the less efficient substrate. After 24 h, more than 90% of the initial cholesterol present in all substrates was converted into cholesteryl esters (FIG. 5a). The Lineweaver-Burk plots obtained by plotting 1/Vo as a function of 1/c peptide, are shown on FIG. 6 and in Table 2, indicating that although the Vmax values are comparable for the M1, M4 and 18A phospholipid-peptides, they are about two to three times lower than those for apo AI-phospholipid complexes (Table 2).

M1 and M3-phospholipid complexes give considerably lower Vmax values (Table 2). For all the phospholipid-peptide complexes studied, the M4-phospholipid complexes demonstrate a maximal activity (highest Vm/Km value), which reaches about 37% of the apo AI-phospholipid activating capacity. This activity is significantly better than those of the 18A peptide and the M1, M2 and M3 peptides.

Induction of cellular cholesterol efflux by the peptide-lipid complexes (FIG. 7)

The J774 macrophages were loaded with acetylated LDL as described under "Experimental procedures". The unloaded J774 cells contain about 17 μg unesterified cholesterol and no detectable cholesteryl esters. After 24 h incubation with 100 μg acetylated LDL, the cholesteryl esters represented 50% of the total cellular cholesterol content which had increased from 17 to 80–90 μg/mg cell protein.

During incubation with 100 μg peptide-DPPC complex for 24 h, around 45% of the intracellular cholesteryl esters were hydrolyzed and secreted into the medium together with 40% of the total cellular cholesterol content. Cholesterol efflux into the medium occurred only as free cholesterol as no cholesteryl esters were detected by HPLC in the medium. A reciprocal decrease of the free and esterified cholesterol content of the cells was observed concomitantly. Cholesterylesters can be detected in the medium (i.e. in the complexes) when the peptide-phosholipid complexes were incubated together with a purified LCAT prepration. Addition of this enzyme caused estrification of 70 % of the cholesterol in the complexes.

After 24 h incubation, the amount of cholesterol released into the medium increased as a function of the acceptor concentration. At a protein concentration of the complex in the medium of 100 μg/ml, the M4 and the 18A peptide induced an efflux of 20 ug free cholesterol into the medium, as compared to ±8 ug of cholesterol that showed efflux with the apo AI-phospholipid complex incubated at an equal concentration. The other complexes induced a similar amount of free cholesterol efflux comparable to that of the apoAI complexes.

REFERENCES

Anantharamaiah GM (1986) Synthetic peptide analogs of apolipoproteins. Methods Enzymol 128: 626–668.

Brasseur R, De Meutter J, Vanloo B, Goormaghtigh E, Ruysschaert J M, Rosseneu M (1990) Mode of assembly of amphipathic helical segments in model high density lipoproteins. Biochim Biophys Acta 1043: 245–252.

Brasseur R (1991) Differentiation of lipid-associating helices by use of three-dimensional molecular hydrophobicity potential calculations. J Biol Chem 266: 16120–16127.

Brown M S, Basu S K, Falck J R, Ho Y K, Goldstein J L (1980). The scavenger cell pathway for lipoprotein degradation. Specificity of the binding site that mediates the uptake of negatively-charged LDL by macrophages. J Supramol Struct 13: 67–81.

Brown M S, Goldstein J L (1986) A receptor mediated pathway for cholesterol homeostasis. Science 232: 34–47.

Compton L A, Jr. Johnson W C (1986) Analysis of protein circular dichroism spectra for secondary structure using a simple matrix multiplication. Anal Biochem 155: 155–167.

Delamatre J, Wolfbauer G, Phillips M C, Rothblat G H (1986) Role of apolipoprotein in cellular cholesterol efflux. Biophys Acta 875: 419–428.

De Loof H, Rosseneu M, Brasseur R, Ruysschaert J M (1987) Functional differentiation of amphiphilic helices of the apolipoproteins by hydrophobic moments analysis. Biochim Biophys Acta 911: 45–52.

Epand R M, Surewicz W K, Hughes D W et al. (1989) Properties of lipid complexes with amphipathic helix-forming peptides. J Biol Chem 264: 4628–4635.

Eisenberg D (1984) Three-dimensional structure of membrane and surface proteins. Ann Rev Biochem 53: 595–623.

Eisenberg D, Weiss R M, Terwilliger T C (1984) The hydrophobic moment detects periodicity in the protein hydrophobicity. Proc Natl Acad Sci USA 81: 140–144.

Fukushima D, Yokoyama S, Kroon D J, Kezdy D J, Kaiser E T (1980) Chain-length function correlation of amphilic peptides. Synthesis and surface properties of a tetracontapeptide segment of apolipoprotein A-I. J Biol Chem 255: 10651–10657.

Gianturco S H, Bradley W A (1987) Lipoprotein receptors. In: Gotto A M. Plasma lipoproteins. Amsterdam, Elsevier: 183–220.

Goormaghtigh E, De Meutter D, Vanloo B, Brasscur R, Rosseneu M, Ruysschaert J M (1989) Evaluation of the secondary structure of apo B-100 in low density lipoprotein (LDL) by infrared spectroscopy. Biochim Biophys Acta 1006: 147–150.

Jonas A (1987) Lecithin cholesterol acyl transferase. In:Gotto A M. Plasma lipoproteins. Amsterdam, Elsevier: 299–333.

Kanellis P, Romans A Y, Johnson B J, et al. (1980) Studies of synthetic peptide analogs of the amphipathic helix. Effect of charged amino acid residue topography on lipid affinity. J Biol Chem 255:11464–11472.

Kovanen P T, Frick M H, Manninen V (1990) Lipoproteins and the pathobiology of the arterial wall. Eur Heart J 11 (suppl E): 1–246.

Levine D M, Parker T S, Donelly T M, Walsh A M, Rubin A L (1992) Mice with high plasma concentrations of High Density Lipoprotein are resistant to the lethal consequences of endotoxic shock. Abstract to the American Heart Meetinf, New Orleans 1992, p. 114.

Lowry O H, Rosebrough N J, Farr A L, Randall R J (1951) Protein measurement with the folin phenol reagent. J Biol Chem 193: 265–275.

Phillips M C, Johnson W J, Rothblat G H (1987) Mechanisms and consequences of cellular cholesterol exchange and transfer. Biochim Biophys Acta 906: 223–276.

Pownall H J, Hu A, Gotto A M, Albers J J, Sparrow J T (1980) Activation of lecithin cholesterol acyltransferase by synthetic model lipid-associating peptide. Proc Natl Acad Sci USA 77: 3154–3158.

Pownall H J, Massey J B, Sparrow J T, Gotto A M (1987) Lipid-protein interactions and lipoprotein reassembly. In: Gotto A M. Plasma Lipoproteins. Amsterdam, Elsevier: 95–127.

Scholtz J., Baldwin R. (1992) The mechanism of α-helix formation by peptides. Annual Review Biophys. Biomol. Structure 21: 95–118.

Segrest I P, Chung B H C. G. Brouillette C G, Kanellis P, McGahan R (1983) Studies of synthetic peptide analogs of the amphipathic helix. Competitive displacement of exchangeable apolipoproteins from native lipoproteins. J Biol Chem 258: 2290–2295.

Segrest I P, De Loof H, Dohlman J G, Brouillette C G, Anantharamaiah G M (1990) Amphipathic helix motif: classes and properties. Proteins 8: 103–117.

Sparrow J T, Gotto A M (1981) Apolipoprotein/lipid interaction: studies with synthetic polypeptides. Crit Rev Biochem 13: 87–107.

Vanloo B, Morrison J, Fidge N, et al. (1991) Characterization of the discoidal complexes formed between apo AI-CNBr fragments and phosphatidylcholine. J Lipid Res 32: 1253–1264.

Vercaemst R, Union A, Rosseneu M (1989) Separation and quantitation of free cholesterol and cholesteryl esters in a macrophage cell line by high-performance liquid chromatography. J Chromatography 494: 43–52.

Wilson C, Wardell M R, Weisgraber K H, Mahley R W, Agard DA (1991) Three-dimensional structure of the LDL receptor-binding domain of human apolipoprotein E. Science 252: 1817–1822.

---

We claim:

1. A peptide comprising the following sequence of amino acids:

Glu-Trp-Leu-A-Ala-B-Tyr-C-Lys-Val-D-Glu-Lys-Leu-Lys-Glu-Leu-Phe, wherein A is Lys, Glu or Asp;

B is Phe, Glu or Asp;

C is Glu, Lys or Arg; and

D is Leu, Glu or Asp;

provided that said peptide is not Glu-Trp-Leu-Lys-Ala-Phe-Tyr-Glu-Lys-Val-Leu-Glu-Lys-Glu-Leu-Phe.

2. The peptide according to claim 1, wherein said peptide is able to bind or to associate with phospholipids, or with phospholipids and cholesterol, to form a discoidal complex.

3. The peptide according to claim 2, wherein said peptide is capable of forming a phospholipid-peptide complex, said complex containing from about 15 to about 25 of said peptides, said complex having a thickness of about 38 Å to about 42 Å, and a diameter of about 80 Å to about 150 Å.

4. The peptide according to claim 1, wherein said peptide is dimeric in form.

5. The peptide according to claim 1, wherein when said peptide forms a complex with phospholipids, and optionally with cholesterol, said peptide can activate lecithin cholesterol acyl transferase (LCAT) in an amount not less than about 10% of the LCAT activation by complexes prepared with native plasma apo AI (purified from human plasma)-phospholipid complexes.

6. The peptide according to claim 1, wherein:

when said peptide is associated in a complex with phospholipids, and optionally with cholesterol, said peptide is stable against GdmCl denaturation, up to 4M of GdmCl, measured according to Trp fluorescence emission, after excitation at 295 nm, said peptide has a binding capacity for phospholipids from about 3 moles of phospholipids/mole of peptide to about 9 moles of phospholipids/mole of peptide, said peptide has an alpha-helical content increase such that the difference between the free peptide and the phospholipid-complex is of at least 15% measured by infrared spectroscopy or circular dichroism.

7. The peptide according to claim 1, wherein said peptide induces a maximal cholesterol efflux under the form of free cholesterol from cholesterol-loaded cells of about 20 µg to 25 µg of free cholesterol, at a peptide concentration of the complex of about 100 µg/ml.

8. The peptide according to claim 1, comprising at least one sequence selected from the group consisting of:

M1 Glu-Trp-Leu-Lys-Ala-Phe-Tyr-Lys-Lys-Val-Leu Glu-Lys-Leu-Lys-Glu-Leu-Phe (SEQ ID NO 1)

M2 Glu-Trp-Leu-Lys-Ala-Glu-Tyr-Glu-Lys-Val-Leu-Glu-Lys-Leu-Lys-Glu-Leu-Phe (SEQ ID NO 2)

M3 Glu-Trp-Leu-Lys-Ala-Glu-Tyr-Glu-Lys-Val-Glu-Glu-Lys-Leu-Lys-Glu-Leu-Phe (SEQ ID NO 3) and M4 Glu-Trp-Leu-Glu-Ala-Phe-Tyr-Lys-Lys-Val-Leu-Glu-Lys-Leu-Lys-Glu-Leu-Phe (SEQ ID NO:4).

9. A phospholipid-protein complex containing at least one peptide of claim 1, phospholipids and optionally cholesterol.

10. A phospholipid-protein complex according to claim 9, which presents a turbidity decrease with respect to DMPC (dimyristoylphosphatidylcholine) of about 0.7 to about 0.05 at 340 nm when said complex is mixed with multilamellar DMPC liposomes and the mixture is heated from 15 ° C. to 25 ° C.

11. A phospholipid-protein complex according to claim 9, wherein said at least one peptide is stacked upon another.

12. A phospholipid protein complex according to claim 9, wherein said phospholipid is selected from the group consisting of:

DMPC (dimyristoylphosphatidylcholine),

DPPC (dipalmitoylphosphatidylcholine),

POPC (palmitoyloleolylphosphatidylcholine),

PLPC (palmitoyllinoleylphosphatidylcholine) and, egg PC (egg phosphatidylcholine).

13. A process for preparing a phospholipid-protein complex, comprising incubating the peptide according to claim 1, with phospholipids, and optionally cholesterol, in the presence of a detergent to obtain a phospholipidprotein complex, and subsequently conducting dialysis of the detergent and fractionation of said complex in order to remove free protein, free phospholipids or free cholesterol.

14. A pharmaceutical composition, comprising a phospholipid-protein complex according to claim 9 and a physiologically appropriate pharmaceutical vehicle.

15. A pharmaceutical composition according to claim 14, containing from about 10 to about 125 mg of phospholipid-protein complex per kg of body weight.

16. A method of treating cardiovascular disease in a mammal comprising administering to a mammal in need of such treatment the peptide according to claim 1.

17. A method of reducing the inducting progression and inducing regression of atherosclerotic plaques in a mammal comprising administering to a mammal in need of such treatment, the phospholipid-protein complex according to claim 9.

18. A method of treating cardiovascular disease in a mammal comprising administering to the mammal in need of such treatment a phospholipid-protein complex according to claim 9.

19. The peptide as in claim 1 wherein said peptide is coiled in the form of an alpha helix having from 2 to 8 turns, each turn bearing 3.6 amino acid residues, the diameter of said helix is from about 13 Å to about 16 Å, the distance separating two consecutive turns of said helix being from about 4 Å to about 6 Å, the length of the helix being from about 10 Å to about 30 Å, said peptide is amphipathic, the value of the hydrophobic pho angle is from about 120° to about 180°, the value of the hydrophilic phi angle is from about 180° to about 240°.

20. The peptide as in claim 19 wherein said peptide is coiled in the form of an alpha helix having 5 turns, each turn bearing 3.6 amino acid residues, the diameter of said helix is about 15 Å, the distance separating two consecutive turns of said helix is about 5 Å, the length of the helix is about 24 Å to about 26 Å, the value of the hydrophobic pho angle is from about 140° to about 180°, and the value of the hydrophilic phi angle is from about 180° to about 220°.

21. The peptide as in claim 4 wherein said peptide is linked by a beta-strand structure containing 5 amino acids including a proline at position 3 from the N or C terminal.

22. The peptide as in claim 4 wherein said peptide is closed by a sequence situated at the C- or N- terminal end.

23. A phospholipid-protein complex as in claim 9 wherein the amount of phospholipids is from about 3 to about 9 moles per mole of said peptide, and the amount of cholesterol being from 0 to 10% with respect to the amount of phospholipids (w/w).

24. A phospholipid-protein complex as in claim 23 having a molar ratio of phospholipids, with respect to peptide, varying from 2/1 to 4/1.

25. A phospholipid-protein complex as in claim 12 wherein said phospholipid is DPPC.

26. A peptide comprising the sequence of amino acids:

Glu-Trp-Leu-A-Ala-B-Tyr-C-Lys-Val-D-Glu-Lys-Leu-Lys-Glu-Leu-Phe, wherein:

A is Lys, Glu or Asp,

B is Phe, Glu or Asp,

C is Glu, Arg or Lys, and

D is Leu, Glu or Asp, and wherein peptide:

is coiled in the form of an alpha helix having from 2 to 8 turns, each turn bearing 3.6 amino acid residues, the diameter of said helix is from about 13 Å to about 16 Å, the distance separating two consecutive turns of said helix being from about 4 Å to about 6 Å, the length of the helix from about 10 Å to about 30 Å, said peptide is amphipatic, the value of the hydrophobic pho angle is from about 120° to about 180°, and the value of the hydrophilic phi angle is from about 180° to about 140°, provided that said peptide is not Glu-Trp-Leu-Lys-Ala-Phe-Tyr-Glu-Lys-Val-Leu-Glu-Lys-Leu-Lys-Glu-Leu-Phe.

27. A method of treating endotoxic shock in a mammal comprising administering to a mammal in need of such treatment the peptide according to claim 1.

28. A method of treating endotoxic shock in a mammal comprising administering to a mammal in need of such treatment the phospholipid-protein complex according to claim 8.

29. A composition comprising the peptide of claim 1 and a pharmaceutically acceptable carrier.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( x i ) SEQUENCE DESCRIPTION: SEQ ID NO: 1:

```
Glu Trp Leu Lys Ala Phe Tyr Lys Lys Val Leu Glu Lys Leu Lys Glu
1               5                   10                  15
Leu Phe
```

( 2 ) INFORMATION FOR SEQ ID NO: 2:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( x i ) SEQUENCE DESCRIPTION: SEQ ID NO: 2:

```
Glu Trp Leu Lys Ala Glu Tyr Glu Lys Val Leu Glu Lys Leu Lys Glu
1               5                   10                  15
Leu Phe
```

( 2 ) INFORMATION FOR SEQ ID NO: 3:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( x i ) SEQUENCE DESCRIPTION: SEQ ID NO: 3:

| Glu | Trp | Leu | Lys | Ala | Glu | Tyr | Glu | Lys | Val | Glu | Glu | Lys | Leu | Lys | Glu |
|---|---|---|---|---|---|---|---|---|---|---|---|---|---|---|---|
| 1 | | | | 5 | | | | | 10 | | | | | 15 | |

Leu  Phe ( 2 ) INFORMATION FOR SEQ ID NO: 4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( x i ) SEQUENCE DESCRIPTION: SEQ ID NO: 4:

| Glu | Trp | Leu | Glu | Ala | Phe | Tyr | Lys | Lys | Val | Leu | Glu | Lys | Leu | Lys | Glu |
|---|---|---|---|---|---|---|---|---|---|---|---|---|---|---|---|
| 1 | | | | 5 | | | | | 10 | | | | | 15 | |

Leu  Phe